(12) United States Patent
Amundson et al.

(10) Patent No.: US 7,597,954 B2
(45) Date of Patent: Oct. 6, 2009

(54) SUPERSATURATED SOLUTIONS USING CRYSTALLIZATION ENTHALPY TO IMPACT TEMPERATURE CHANGE TO WET WIPES

(75) Inventors: John David Amundson, Greenville, WI (US); Kambiz Bayat Makoui, Neenah, WI (US); Frank P. Abuto, Duluth, GA (US); David Martin Jackson, Alpharetta, GA (US); Jenny L. Day, Woodstock, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 237 days.

(21) Appl. No.: 11/610,970

(22) Filed: Dec. 14, 2006

(65) Prior Publication Data

US 2008/0145663 A1 Jun. 19, 2008

(51) Int. Cl.
*B32B 3/26* (2006.01)
*B32B 27/04* (2006.01)

(52) U.S. Cl. .............. 428/321.1; 428/320.2; 428/321.5; 442/123; 442/170; 442/171

(58) Field of Classification Search ................ 442/170, 442/171, 123; 428/320.2, 321.1, 321.5
See application file for complete search history.

(56) References Cited

U.S. PATENT DOCUMENTS

| | | | |
|---|---|---|---|
| 1,312,449 A | 8/1919 | Lundberg |
| 2,766,478 A | 10/1956 | Raley, Jr. et al. |
| 3,016,308 A | 1/1962 | Macaulay |
| 3,084,664 A | 4/1963 | Solomon et al. |
| 3,175,558 A | 3/1965 | Caillonette et al. |
| 3,199,490 A | 8/1965 | Karlik |
| 3,261,347 A | 7/1966 | Sherman |
| 3,310,353 A | 3/1967 | Cordis |
| 3,363,604 A | 1/1968 | Pschibul |
| 3,388,953 A | 6/1968 | Browning |
| 3,429,827 A | 2/1969 | Ruus |
| 3,441,353 A | 4/1969 | Claff |
| 3,464,413 A | 9/1969 | Goldfarb, et al. |
| 3,472,675 A | 10/1969 | Gordon, et al. |
| 3,516,941 A | 6/1970 | Matson |
| 3,585,982 A | 6/1971 | Hollinshead |
| 3,674,176 A | 7/1972 | Sagi |
| 3,691,090 A | 9/1972 | Kitajima et al. |
| 3,691,270 A | 9/1972 | Charle et al. |
| 3,839,220 A | 10/1974 | Barchas |

(Continued)

FOREIGN PATENT DOCUMENTS

DE 29809967 U1 10/1998

(Continued)

OTHER PUBLICATIONS

Non-final Office Action regarding U.S. Appl. No. 11/320,369 (Jan. 27, 2009).

(Continued)

*Primary Examiner*—Lynda Salvatore
(74) *Attorney, Agent, or Firm*—Armstrong Teasdale LLP

(57) ABSTRACT

Personal care products comprising supersaturated solutions and core compositions comprising activation means are disclosed. In one embodiment, a core composition comprising the activation means is surrounded by an encapsulation layer. The core composition comprising the activation means may be introduced into wet wipes such that, upon rupture and contact between the supersaturated solution and the activation means, the wet wipe solution is warmed resulting in a warm sensation on a user's skin. Any number of other active ingredients, such as biocides, can also be incorporated into the personal care product.

20 Claims, 6 Drawing Sheets

U.S. PATENT DOCUMENTS

| | | | |
|---|---|---|---|
| 3,854,624 A | 12/1974 | Canci | |
| 3,862,715 A | 1/1975 | Remenyik | |
| 3,889,804 A * | 6/1975 | Ravich | 206/221 |
| 3,947,571 A | 3/1976 | Murphy et al. | |
| 3,982,659 A | 9/1976 | Ross | |
| 4,004,711 A | 1/1977 | Ravich | |
| 4,036,301 A | 7/1977 | Powers et al. | |
| 4,077,390 A | 3/1978 | Stanley et al. | |
| 4,088,751 A | 5/1978 | Kenkare et al. | |
| 4,460,563 A | 7/1984 | Calanchi | |
| 4,504,402 A | 3/1985 | Chen | |
| 4,505,953 A | 3/1985 | Chen | |
| 4,513,053 A | 4/1985 | Chen | |
| 4,568,559 A | 2/1986 | Nuwayser et al. | |
| 4,853,266 A | 8/1989 | Cullen | |
| 4,872,442 A | 10/1989 | Manker | |
| 4,880,953 A | 11/1989 | Manker | |
| 4,923,645 A | 5/1990 | Tsang et al. | |
| 5,184,613 A | 2/1993 | Mintz | |
| 5,187,011 A | 2/1993 | Manalastas | |
| 5,192,615 A | 3/1993 | McDougall | |
| 5,204,183 A | 4/1993 | McDougall | |
| 5,232,769 A | 8/1993 | Yamato et al. | |
| 5,339,796 A | 8/1994 | Manker | |
| 5,350,624 A | 9/1994 | Georger et al. | |
| 5,366,801 A | 11/1994 | Bryant et al. | |
| 5,375,616 A | 12/1994 | Chen | |
| 5,385,737 A | 1/1995 | Shigeno et al. | |
| 5,392,945 A | 2/1995 | Syrek | |
| 5,401,601 A | 3/1995 | Sacripante et al. | |
| 5,415,222 A | 5/1995 | Colvin et al. | |
| 5,425,975 A | 6/1995 | Koiso et al. | |
| 5,435,465 A | 7/1995 | El-Amin | |
| 5,462,197 A | 10/1995 | Pound | |
| 5,589,194 A | 12/1996 | Tsuei et al. | |
| 5,697,577 A | 12/1997 | Ogden | |
| 6,021,920 A | 2/2000 | Aldape | |
| 6,063,406 A | 5/2000 | Hornack | |
| 6,099,555 A | 8/2000 | Sabin | |
| 6,238,682 B1 | 5/2001 | Klofta et al. | |
| 6,314,971 B1 | 11/2001 | Schneider | |
| 6,319,318 B1 | 11/2001 | Pekarek et al. | |
| 6,321,937 B1 | 11/2001 | Desimone et al. | |
| 6,322,801 B1 | 11/2001 | Lorenzi et al. | |
| 6,343,491 B1 | 2/2002 | Jung | |
| 6,346,153 B1 | 2/2002 | Lake et al. | |
| 6,355,281 B1 | 3/2002 | Cerchiari et al. | |
| 6,387,385 B1 | 5/2002 | Wang | |
| 6,401,968 B1 | 6/2002 | Huang et al. | |
| 6,562,318 B1 | 5/2003 | Filler | |
| 6,579,570 B1 | 6/2003 | Lang et al. | |
| 6,726,386 B1 | 4/2004 | Gruenbacher et al. | |
| 6,952,849 B2 | 10/2005 | Pacella | |
| 7,101,612 B2 | 9/2006 | Lang et al. | |
| 7,108,440 B1 | 9/2006 | Gruenbacher et al. | |
| 7,211,249 B2 | 5/2007 | Schnittger et al. | |
| 7,229,611 B2 | 6/2007 | Zamudio-Tena et al. | |
| 7,238,655 B2 | 7/2007 | Ness | |
| 2002/0044968 A1 | 4/2002 | van Lengerich | |
| 2002/0102488 A1 | 8/2002 | Yanaka et al. | |
| 2002/0155281 A1 | 10/2002 | Lang et al. | |
| 2002/0174863 A1 | 11/2002 | Saric et al. | |
| 2003/0082217 A1 | 5/2003 | Afriat et al. | |
| 2003/0084914 A1 | 5/2003 | Simon | |
| 2003/0198652 A1 | 10/2003 | Shefer et al. | |
| 2003/0228351 A1 | 12/2003 | Hassenoehrl et al. | |
| 2004/0062735 A1 | 4/2004 | Sun et al. | |
| 2004/0063603 A1 | 4/2004 | Dave et al. | |
| 2004/0069298 A1 | 4/2004 | Minami | |
| 2004/0116017 A1 | 6/2004 | Smith, III et al. | |
| 2005/0136765 A1 | 6/2005 | Shannon | |
| 2005/0214242 A1 | 9/2005 | Mohammadi et al. | |
| 2006/0018953 A1 | 1/2006 | Guillon et al. | |
| 2006/0159776 A1 | 7/2006 | Ward | |
| 2007/0027415 A1 | 2/2007 | Kopreski | |

FOREIGN PATENT DOCUMENTS

| | | |
|---|---|---|
| DE | 19846375 A1 | 4/2000 |
| DE | 10205872 A2 | 3/2003 |
| DE | 10209111 A1 | 9/2003 |
| DE | 20305272 | 9/2003 |
| DE | 10361100 A1 | 1/2005 |
| EP | 1084670 A2 | 3/2001 |
| EP | 1310186 | 5/2003 |
| EP | 1402879 | 3/2004 |
| EP | 1407762 | 4/2004 |
| GB | 1291377 | 10/1972 |
| GB | 2168031 A | 6/1986 |
| GB | 2192171 A | 1/1988 |
| JP | 08067869 | 3/1996 |
| JP | 08067869 A | 3/1996 |
| JP | 09047376 | 2/1997 |
| JP | 10077134 | 3/1998 |
| JP | 2003104465 | 4/2003 |
| WO | 9322961 A1 | 11/1993 |
| WO | 02026911 A | 4/2002 |
| WO | 2004105709 A1 | 12/2004 |
| WO | 2005018794 | 3/2005 |
| WO | 2005093029 | 10/2005 |

OTHER PUBLICATIONS

Non-final Office Action regarding U.S. Appl. No. 11/319,881, dated Feb. 6, 2009.

Non-final Office Action regarding U.S. Appl. No. 12/174,459, dated Feb. 5, 2009.

Non-final Office Action, U.S. Appl. No. 11/420,988 (Feb. 25, 2009).

Non-final Office Action, U.S. Appl. No. 11/320,363 (Mar. 3, 2009).

Non-final Office Action from U.S. Appl. No. 11/320,049, dated May 4, 2009.

Non-final Office Action, U.S. Appl. No. 11/420,980 (Mar. 12, 2009).

Non-final Office Action regarding U.S. Appl. No. 11/610,980, dated Feb. 26, 2009.

Office Action regarding U.S. Appl. No. 11/319,953, dated Dec. 12, 2008.

Non-final Office Action, U.S. Appl. No. 11/609,701 (Apr. 2, 2009).

Non-final Office Action, U.S. Appl. No. 11/319,853 (Apr. 1, 2009).

Non-final Office Action, U.S. Appl. No. 11/320,247 (Apr. 3, 2009).

Final Office Action regarding U.S. Appl. No. 11/319,953, dated Apr. 28, 2009.

Non-final Office Action from U.S. Appl. No. 11/610,985, dated Jun. 8, 2009.

International Cosmetic Ingredient Dictionary and Handbook, 10th Ed., vol. 3, pp. 2294-2296 (2004).

Araki et al., "Measurements of Thermophysical Properties of Sodium Acetate Hydrate," International J. of Thermo., 16 (6): 1455-1466 (1995).

K. Sturley, "Fresh Data on the Latent Heats and Heat conductivities of Some Aqua-Crystalline Compounds," J. of the Society of Chem. Industr., 51:271T-273T (Aug. 12, 1932).

Chatterji et al., "The Rate of Crystal Growth in Supersaturated Solutions, Part I," J. Indian Chem. Soc., 28(12): 599-601 (Dec. 1951).

M. Telkes, "Nucleation of Supersaturated Inorganic Salt Solutions," Industrial and Engineering Chemistry, 44/6: 1308-1310 (Jun. 1952).

Dietz, Jr. et al., "Linear Crystallization Velocities of Sodium Acetate in Supersaturated Solutions," J. Phys. Chem., 61(7): 944-948 (Jul. 1957).

Meisingset, et al., "Thermodynamic Properties and Phase Transitions of Salt Hydrates between 270 and 400 K," J. Chem. Thermodynamics, 16(1-6): 523-536 (Jan. 1984).

Wada, et al., "Heat Storage Capacity of Sodium Acetate Trihydrate during Thermal Cycling," Solar Energy, 33(3/4): 373-375 (1984).

J.C. Deelman, Mechanism of formation of Magnesite and Dolomite, Ch. 8, pp. 278-329 (2003).

Rogerson, et al., "Solidification of Heat Packs: 1. Nucleation Rate," AIChE Journal, 49(2): 505-529 (Feb. 2003).

A.V. Patel, et al. "A Novel Encapsulation Technique for the Production of Artificial Seeds," Plant Cell Reports, 19:868-874 (2000).

International Search Report for PCT/US2006/039137 dated Mar. 23, 2007.

International Search Report for PCT/US2006/042435 dated Mar. 23, 2007.

International Search Report for PCT/US2006/038914 dated Mar. 23, 2007.

International Search Report and Written Opinion from PCT/US2006/038834, dated Apr. 11, 2007.

International Search Report and Written Opinion from PCT/US2006/038915, dated Apr. 5, 2007.

International Search Report and Written Opinion from PCT/US2006/042050, dated May 2, 2007.

International Search Report for PCT/US2006/038271 dated May 3, 2007.

* cited by examiner

FIBROUS SHEET CONTAINING SUPERSATURATED SOLUTION AND ACTIVATION MEANS

COFORM

PLASTIC FILM

MICROCAPSULES CONTAINING ONE OR MORE SEED CRYSTALS

GELLED SUPERSATURATED SOLUTION

COFORM

PLASTIC FILM

MICROCAPSULES CONTAINING ONE OR MORE SEED CRYSTALS

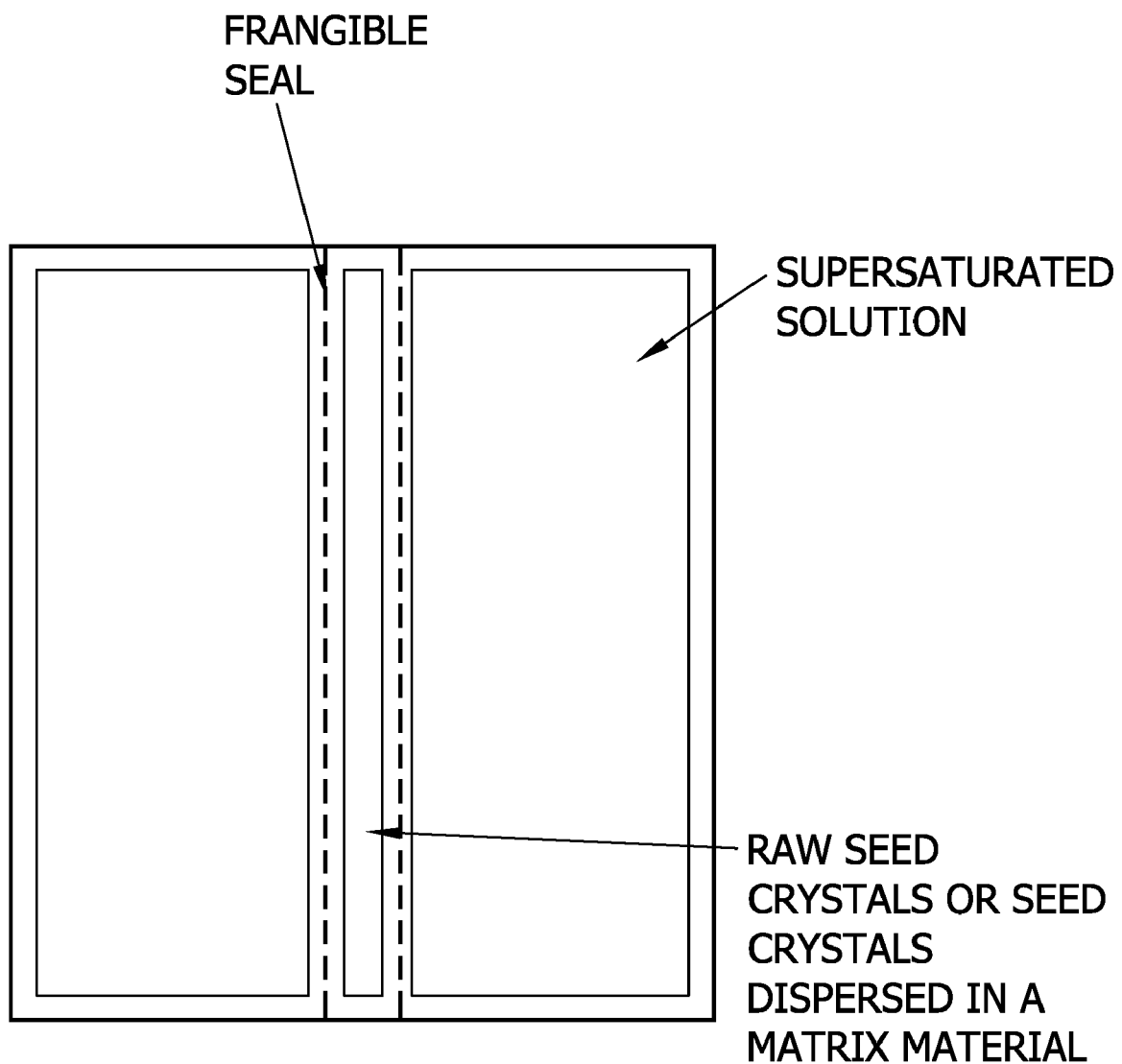

SUPERSATURATED SOLUTIONS USING CRYSTALLIZATION ENTHALPY TO IMPACT TEMPERATURE CHANGE TO WET WIPES

BACKGROUND OF THE DISCLOSURE

The present disclosure relates generally to products incorporating compositions including supersaturated solutions capable of imparting a temperature change to the products through crystallization enthalpy. More particularly, the present disclosure is directed to supersaturated solutions that can be effectively utilized in a wipe or similar product such that, upon use and activation, the supersaturated solutions are contacted with one or more activation means, which causes a warming sensation on the skin upon product use. The products may include one or more other active ingredients.

Wet wipes and dry wipes and related products have been used for some time by consumers for various cleaning and wiping tasks. For example, many parents have utilized wet wipes to clean the skin of infants and toddlers before and after urination and/or defecation. Many types of wet wipes are currently commercially available for this purpose.

Today, many consumers are demanding that personal health care products, such as wet wipes, have the ability to not only provide their intended cleaning function, but also to deliver a comfort benefit to the user. In recent studies, it has been shown that baby wet wipes currently on the market are sometimes perceived to be uncomfortably cold upon application to the skin, particularly for newborns. To mitigate this problem, there have been many attempts to produce warming products to warm the wipes to comfort the wet wipe users from the inherent "chill" given off by the contact of the moistened wipes upon the skin.

These warming products are generally electrically operated and come in two distinct styles. One is an "electric blanket" style which is sized to wrap around the external surfaces of a plastic wet wipes container. The other is a self-contained plastic "appliance" style which warms the wet wipes with its internally positioned heating element. Though such currently known and available wet wipe warming products typically achieve their primary objective of warming the wet wipe prior to use, they possess certain deficiencies, which can detract from their overall utility and desirability.

Perhaps the biggest deficiency of the current wet wipe warming products is their inability to sustain the moisture content of the wet wipes. More specifically, drying of the wet wipes occurs due to heating of their moisture which accelerates dehydration. As a result, wet wipes may become dried-out and unusable.

Other complaints by wipe warmer users include discoloration of the wet wipes after heating, which appears to be inevitable because of a reaction of various chemicals in the wipes upon the application of heat. Wipe warmer users further complain about warmer inconvenience and potential electrical fire hazards, which can result with the use of electrical warming products.

Based on the foregoing, there is a need in the art for wet wipes that can produce a warming sensation just prior to, or at the point of use, without using external heating products. It would be desirable if the wet wipes could produce a warming sensation within less than about 10 seconds after activation and raise the temperature of the wet wipe solution and the wet wipe base substrate at least 20° C. or more for at least 20 seconds.

SUMMARY OF THE DISCLOSURE

The present disclosure relates to supersaturated solutions and activation means, suitable for use in personal care products, such as wet wipes, dry wipes, cloths, and the like. Other active agents may also be employed in the personal care products, such as biocide agents.

In one embodiment, the supersaturated solution, upon contact with an activation means in a wet wipe, for example, can produce a warming sensation on the skin when the wet wipe is used. The supersaturated solution is typically incorporated into a composition and the activation means is typically incorporated into a separate core composition. Optionally, the core composition may also include a matrix material, a surfactant and a wax material surrounding the activation means to improve overall performance. Additionally, the core composition and components therein are optionally encapsulated in a thin capsule that may have one or more moisture protective layers and/or fugitive layers thereon to impart additional advantageous characteristics. Upon use in a wet wipe, the core composition containing the activation means is brought into contact with the supersaturated solution present in the wet wipe and releases heat to cause a warming sensation on the skin.

As such, the present disclosure is directed to a wet wipe comprising a composition comprising a supersaturated solution, and a core composition surrounded by an encapsulation layer. The core composition comprises a matrix material and an activation means.

The present disclosure is further directed to a wet wipe comprising a gelled composition comprising a supersaturated solution and a gelling agent, and a core composition surrounded by an encapsulation layer. The core composition comprises a matrix material and an activation means.

The present disclosure is further directed to a wet wipe comprising a basesheet material, a first fluid-impermeable pouch comprising a composition comprising a supersaturated solution, and a second fluid-impermeable pouch comprising a core composition comprising an activation means.

The present disclosure is further directed to a wet wipe comprising a fibrous sheet material. The fibrous sheet material comprises a composition comprising a supersaturated solution, and a core composition surrounded by an encapsulation layer. The core composition comprises a matrix material and an activation means.

The present disclosure is further directed to a method of producing a wipe. The method comprises encapsulating an activation means within a core composition; and incorporating a composition comprising a supersaturated solution, and the core composition within a basesheet material.

Other features of the present disclosure will be in part apparent and in part pointed out hereinafter.

BRIEF DESCRIPTION OF THE FIGURES

FIG. 4A is a side view of a wet wipe comprising a supersaturated solution being incorporated into two separate pouches and a powdered activation means dispersed in a strip between the two pouches as disclosed in one embodiment of the present disclosure.

DEFINITIONS

Figure 1A:
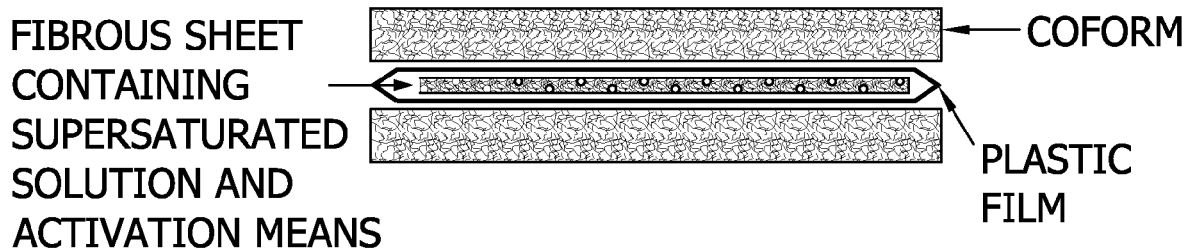
FIG. 1A is a side view of a wet wipe comprising a supersaturated solution and an activation means being incorporated into a fibrous sheet material and further being entrapped between two film layers as disclosed in one embodiment of the present disclosure.

Within the context of this specification, each term or phrase below will include, but not be limited to, the following meaning or meanings:

(a) "Bonded" refers to the joining, adhering, connecting, attaching, or the like, of two elements. Two elements will be considered to be bonded together when they are bonded directly to one another or indirectly to one another, such as when each is directly bonded to intermediate elements.

(b) "Film" refers to a thermoplastic film made using a film extrusion and/or forming process, such as a cast film or blown film extrusion process. The term includes apertured films, slit films, and other porous films which constitute liquid transfer films, as well as films which do not transfer liquid.

(c) "Layer" when used in the singular can have the dual meaning of a single element or a plurality of elements.

(d) "Meltblown" refers to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. (Nov. 19, 1974). Meltblown fibers are microfibers which may be continuous or discontinuous, are generally smaller than about 0.6 denier, and are generally self bonding when deposited onto a collecting surface. Meltblown fibers used in the present disclosure are preferably substantially continuous in length.

(e) "Nonwoven" refers to materials and webs of material which are formed without the aid of a textile weaving or knitting process.

(f) "Polymeric" includes, but is not limited to, homopolymers, copolymers, such as for example, block, graft, random and alternating copolymers, terpolymers, etc. and blends and modifications thereof. Furthermore, unless otherwise specifically limited, the term "polymeric" shall include all possible geometrical configurations of the material. These configurations include, but are not limited to, isotactic, syndiotactic and atactic symmetries.

(g) "Thermoplastic" describes a material that softens when exposed to heat and which substantially returns to a nonsoftened condition when cooled to room temperature.

DETAILED DESCRIPTION OF THE PREFERRED EMBODIMENT

The present disclosure relates to compositions including supersaturated solutions, suitable for use in personal care products such as wet wipes and dry wipes. The present disclosure also relates to self warming wipes that include a supersaturated solution and one or more activation means. The supersaturated solution, upon activation and contact with an activation means, is capable of evolving heat and causing a warming sensation on the skin of a user of the wet wipe. The activation means are included in a core composition that, as described herein, may optionally include one or more encapsulating layers, moisture protective layers, and fugitive layers to impart various characteristics upon the activation means and the products in which they are used. Surprisingly, it has been found that when a supersaturated solution and an activation means are separately incorporated into a wet wipe, and then allowed to come into contact upon wipe use, the wet wipe is warmed to allow for a comforting feel to the skin. In one embodiment, one or more surfactants may also be included with either the composition including the supersaturated solution or the core composition including the activation means, or both in the products. The addition of the surfactant will desirably increase the speed of the dissolution of the core composition (and its components) into the composition including the supersaturated solution. Additional ingredients such as biocide agents may also be included on the surface of the personal care product to produce an improved cleansing product such as a biocidal wet wipe.

Although discussed primarily herein in relation to warming by contacting the supersaturated solution with an activation means, it will be recognized by one skilled in the art based on the disclosure herein that other active agents or active ingredients, in addition to, the supersaturated solution and activation means, may be incorporated into the wet wipes described herein. For example, the wet wipes may include a biocide agent with the supersaturated solution and activation means.

As noted above, the wet wipes contain a composition comprising a supersaturated solution. Supersaturated solutions can be formed by heating aqueous solutions to a temperature of suitably from about 30° C. (86° F.) to about 100° C. (212° F.), and more suitably, from about 32° C. (90° F.) to about 90° C. (194° F.), and dissolving particles (e.g., salts or sugars) in the heated aqueous solutions. Typically, the aqueous solutions are made up of water. Under these heated conditions, more particles are capable of dissolving in the solutions, thereby producing supersaturated solutions. These supersaturated solutions are unstable and will completely crystallize if exposed to an activation means such as a nucleation site (e.g., a seed crystal) as described more fully below. As the solute from the supersaturated solution crystallizes, heat is produced through crystallization enthalpy or latent heat of fusion.

Suitable supersaturated solutions, therefore, are capable of producing a high crystallization enthalpy and a high crystallization rate. Generally, the supersaturated solutions are capable of generating a crystallization enthalpy of at least about 70 Joules/gram, and more suitably at least about 125 Joules/gram. In one embodiment, the supersaturated solutions are capable of generating a crystallization enthalpy of from about 70 Joules/gram to about 500 Joules/gram. Additionally, the supersaturated solutions suitably produce a crystallized solid product having a crystallization rate, that is the rate at which the solution crystallizes, of at least about 0.01 centimeters/second, more suitably at least about 0.03 centimeters/second, even more suitably, at least about 0.05 centimeters/second, and even more suitably at least about 0.10 centimeters/second.

Additionally, the supersaturated solution for use in the wet wipes of the present disclosure suitably has a crystallization temperature of from about 25° C. (77° F.) to about 90° C. (194° F.). More suitably, the supersaturated solution has a crystallization temperature of from about 30° C. (86° F.) to about 60° C. (140° F.). Supersaturated solutions with these crystallization temperatures are capable of warming the wipe to a level of giving the perception of warmth without overheating the wipe to risk skin burns.

One particularly suitable example is a supersaturated solution of sodium acetate. Specifically, to produce a supersaturated solution of sodium acetate, a solution of sodium acetate and water is heated to a temperature of greater than about 58° C. (136.4° F.) and allowed to slowly cool to room temperature. The resulting supersaturated solution of sodium acetate will crystallize once it comes into contact with an activation means such as a sodium acetate seed crystal. The supersaturated sodium acetate solution is capable of generating a crystallization enthalpy of 264 Joules/gram, and thus, will produce a temperature to heat the wet wipe of from about 50° C. (122° F.) to about 60° C. (140° F.). The generation of this amount of heat will generally lead to an increase in wet wipe temperature of approximately 15° C. (27° F.) to 20° C. (36° F.). Additionally, the supersaturated solution will produce a crystallized product, sodium acetate trihydrate, having a crystallization rate of as high as about 0.68 centimeters/second.

Other suitable supersaturated solutions for use in the wet wipes of the present disclosure include, for example, supersaturated solutions prepared from aqueous solutions of salts or sugars, the salt or sugar being selected from the group consisting of sodium sulfate, sodium thiosulfate, potash alum, calcium nitrate, potassium acetate, ammonium nitrate, potassium nitrate, lithium acetate, magnesium acetate, chromium alum, sodium carbonate, magnesium sulfate, sodium borate, sodium bromide, xylitol, sodium chromate, calcium chloride, magnesium chloride, magnesium nitrate, disodium phosphate, urea nitrate, and hydrates thereof.

Typically, the wet wipe should comprise from about 3.0 grams per square meter to about 850 grams per square meter of the composition comprising the supersaturated solution. More typically, the wet wipe should comprise from about 30 grams per square meter to about 330 grams per square meter of the composition, and even more suitably, from about 100 grams per square meter to about 210 grams per square meter.

The supersaturated solution typically present in the composition in an amount of from about 70% (by weight composition) to about 99.9% (by weight composition). More suitably, the supersaturated solution is present in the composition in an amount of from about 90% (by weight composition) to about 99.5% (by weight composition), and even more suitably, from about 93% (by weight composition) to about 99% (by weight composition). As such, the wet wipe should comprise from about 3.0 grams per square meter to about 600 grams per square meter supersaturated solution. More suitably, the wet wipe should include from about 30 gram per square meter to about 300 grams per square meter supersaturated solution, and even more suitably, from about 100 grams per square meter to about 200 grams per square meter supersaturated solution.

Additionally, as noted above, when the supersaturated solution is a supersaturated salt solution, the supersaturated salt solution is produced by dissolving salt in an aqueous solution. Suitably, the salt is present in the aqueous solution in an amount of from about 33% (by weight solution) to about 60% (by weight solution). In one particularly preferred embodiment, the supersaturated salt solution is a supersaturated sodium acetate salt solution comprising from about 45% (by weight solution) to about 58% (by weight solution) sodium acetate. More suitably, the sodium acetate is present in the supersaturated salt solution in an amount of from about 50% (by weight solution) to about 54% (by weight solution).

When the supersaturated solution is a supersaturated sugar solution, the supersaturated sugar solution is produced by dissolving sugar in an aqueous solution. Suitably, the sugar is present in the aqueous solution in an amount of from about 33% (by weight solution) to about 60% (by weight solution).

In one embodiment, the composition comprising the supersaturated solution further includes a gelling agent, wherein upon contact between the supersaturated solution and the gelling agent, a gelled composition is formed. By forming a gelled composition, the supersaturated solution can be evenly distributed within the personal care product without using an additional support layer such as a fibrous sheet as described in the embodiment below. Suitably, the supersaturated solution is present in the gelled composition in an amount of from about 70% (by weight gelled composition) to about 99.9% (by weight gelled composition). More suitably, the supersaturated solution is present in the gelled composition in an amount of from about 90% (by weight gelled composition) to about 99.5% (by weight gelled composition), and even more suitably from about 93% (by weight gelled composition) to about 99% (by weight gelled composition).

In the embodiment using a gelled composition, the gelled composition is present in the wet wipe in an amount of from about 3.0 grams/square meter to about 850 grams/square meter. More suitably, the gelled composition is present in the wet wipe in an amount of from about 30 gram/square meter to about 330 grams/square meter, and even more suitably, from about 100 grams/square meter to about 210 grams/square meter.

As noted above, in addition to the supersaturated solution, the gelled composition includes a gelling agent. Any gelling agent known in the art suitable for gelling the composition may be used in the present disclosure. For example, suitable gelling agents include fumed silica and laponite clay. Additional gelling agents are described in U.S. Pat. Nos. 5,058,563, issued to Charles Manker (Oct. 22, 1991) and 5,339,796, issued to Charles Manker (Aug. 23, 1994), which are both hereby incorporated by reference in their entireties to the extent they are consistent herewith.

Additionally, viscosity increasing agents are suitable for use as gelling agents. Suitable viscosity increasing agents include aqueous viscosity increasing agents, for example, acetamide MEA, acrylamide copolymers, acrylamide/sodium acrylate copolymer, acrylamide/sodium acryloyldimethyltaurate copolymer, acrylates/acetoacetoxyethyl methacrylate copolymer, acrylates/beheneth-25 methacrylate copolymer, acrylates/C10-C30 alkyl acrylate crosspolymer, actylates/ceteth-20 itaconate copolymer, acrylates/ceteth-20 methacrylate copolymer, actylates/laureth-25 methacrylate, acrylates/pameth-25 acrylate copolymer, acrylates/palmeth- 25 itaconate copolymer, acrylates/steareth-50 acrylate copolymer, acrylates/steareth-20 itaconate copolymer, acrylates/steareth-20 methacrylate copolymer, acrylates/stearyl methacrylate copolymer, acrylates/vinyl isodecanoate crosspolymer, acrylic acid/acrylonitrogens copolymer, adipic acid/methyl DEA crosspolymer, agar, agarose, *alcaligenes* polysaccharides, algin, alginic acid, almondamide DEA, almondamidopropyl betaine, aluminum/magnesium hydroxide stearate, ammonium acrylates/acrylonitrogens copolymer, ammonium acrylates copolymer, ammonium acryloyldimethyltaurate/vinyl formamide copolymer, ammonium acryloyldimethyltaurate/VP copolymer, ammonium alginate, ammonium chloride, ammonium polyacryloyldimethyl taurate, ammonium sulfate, amylopectin, apricotamide DEA, apricotamidopropyl betaine, arachidyl alcohol, *Arachis hypogaea* (Peanut) flour, ascorbyl methylsilanol pectinate, *astragalus* gummifer gum, attapulgite, *Avena sativa* (Oat) kernel flour, avocadamide DEA, avocadamidopropyl betaine, azelamide MEA, babassuamide DEA, babassuamide MEA, babassuamidopropyl betaines, behenamide DEA, behenamide MEA, behenamidopropyl betaine, behenyl betaine, bentonite, butoxy chitosan, caesalpinla spinosa gum, calcium alginate, calcium carboxymethyl cellulose, calcium carrageenan, calcium chloride, calcium potassium carbomer, calcium starch octenylsuccinate, C20-C40 alkyl stearate, canolamidopropyl betaine, capramide DEA, capryl/capramidopropyl betaine, carbomer, carboxybutyl chitosan, carboxymethyl cellulose acetate butyrate, carboxymethyl chitin, carboxymethyl chitosan, carboxymethyl dextran, carboxymethyl hydroxyethylcellulose, carboxymethyl hydroxypropyl guar, carnitine, cellulose acetate propionate carboxylate, carnitine, cellulose acetate propionate carboxylate, cellulose gum, ceratonia siliqua gum, cetearyl alcohol, cetyl alcohol, cetyl babassuate, cetyl betaine, cetyl glycol, cetyl hydroxyethylcellulose, chimyl alcohol, cholesterol/HDI/pullulan copolymer, cholesteryl hexyl dicarbamate pullulan, citrus *Aurantium dulois* (Orange) peel extract, cocamide DEA, cocamide MEA, cocamide MIPA, cocamidoethyl betaine, cocamidopropyl betaine, cocamidopropyl hydroxysultaine, coco-betaine, coco-hydroxysultaine, coconut alcohol, coco/oleamidopropyl betaine, coco-sultaine, cocoyl sarcosinamide DEA, cornamide/cocamide DEA, cornamide DEA, croscarmellose, *cyamopsis tetragonoloba* (guar) gum, decyl alcohol, decyl betaine, dehydroxanthan gum, dextrin, dibenzylidene sorbitol, diethanolaminooleamide DEA, diglycol/CHDM/isophthalates/SIP copolymer, dihydroabietyl behenate, dihydrogenated tallow benzylmonium hectorite, dihydroxyaluminum aminoacetate, dimethicone/PEG-15 crosspolymer, dimethicone propyl PG-betaine, DMAPA acrylates/acrylic acid/ acrylonitrogens copolymer, erucamidopropyl hydroxysultaine, ethylene/sodium acrylate copolymer, gelatin, gellan gum, glyceryl alginate, glycine soja (Soybean) flour, guar hydroxypropyltrimonium chloride, hectorite, hyluronic acid, hydrated silica, hydrogenated potato starch, hydrogenated tallow, hydrogenated tallowamide DEA, hydrogenated tallow betaine, hydroxybutyl methylcellulose, hydroxyethyl acrylate/sodium acryloyldimethyl taurate copolymer, hydroxyethylcellulose, hydroxyethyl chitosan, hydroxyethyl ethylcellulose, hydroxyethyl stearamide-MIPA, hydroxylauryl/ hydroxymyristyl betaine, hydroxypropylcellulose, hyroxypropyl chitosan, hydroxylpropyl ethylenediamine carbomer, hydroxypropyl guar, hydroxylpropyl methylcellulose, hydroxylpropyl methylcellulose stearoxy ether, hydroxypropyl starch, hydroxypropyl starch phosphate, hydroxypropyl xanthan gum, hydroxystearamide DEA, isobutylene/sodium maleate copolymer, isostearamide DEA, isostearamide MEA, isostearmaide MIPA, isosteamidopropyl betaine, lactamide MEA, lanolinamide DEA, lauramide DEA, lauramide MEA, lauramide MIPA, lauramide/myristamide DEA, lauramidopropyl betaine, lauramidopropyl hydroxysultaine, lauramino bispropanediol, lauryl alcohol, lauryl betaine, lauryl hydroxysultaine, lauryl sultaine, lecithinamide DEA, linoleamide DEA, linoleamide MEA, linoleaide MIPA, lithium magnesium silicate, lithium magnesium sodium silicate, *Macrocystis pyrifera* (Kelp), magnesium alginate, magnesium/aluminum/hydroxide/carbonate, magnesium aluminum silicate, magnesium silicate, magnesium trisilicate, methoxy PEG-22/dodecyl glycol copolymer, methylcellulose, methyl ethylcellulose, methyl hydroxyethylcellulose, microcrystalline cellulose, milkamidopropyl betaine, minkamide DEA, minkamidopropyl betaine, MIPA-myristate, montmorillonite, moroccan lava clay, myristamide DEA, myristamide MEA, myristamide MIPA, myristamidopropyl betaine, myristamidopropyl hydroxysultaine, myristyl alcohol, myristyl betaine, natto gum, nonoxynyl hydroxylethylcellulose, oatamide MEA, oatamidopropyl betaine, octacosanyl glycol isostearate, octadecene/ma copolymer, oleamide DEA, oleamide MEA, oleamide MIPA, oleamidopropyl betaine, oleamidopropyl hydroxysultaine, oleyl betaine, olivamide DEA, olivamidopropyl hydroxysultaine, oliveamide MEA, palmamide DEA, palmamide MEA, palmamide MIPA, palmamidopropyl betaine, palm kernel alcohol, palm kernelamide DEA, palm kernelamide MEA, palm kernelamide MIPA, palm kernelamidopropyl betaine, peanutamide MEA, peanutamide MIPA, pectin, PEG-800, PEG-crosspolymer, PEG-150/decyl alcohol/SMDI copolymer, PEG-175 dilsostearate, PEG-190 distearate, PEG-15 glyceryl tristearate, PEG-140 glyceryl tristearate, PEG-240/ HDI copolymer bis-decyltetradeceth-20 ether, PEG-100/ IPDI copolymer, PEG-180/laureth-50/TMMG copolymer, PEG-10/lauryl dimethicone crosspolymer, PEG-15/lauryl dimethicone crosspolymer, PEG-2M, PEG-5M, PEG-7M, PEG-9M, PEG-14M, PEG-20M, PEG-23M, PEG-25, PEG-45M, PEG-65M, PEG-90M, PEG-115M, PEG-160M, PEG-120 methyl glucose trioleate, PEG-180/octoxynol-4/TMMG copolymer, PEG-150 pentaerythrityl tetrastearate, PEG-4 rapeseedamide, PEG-150/stearyl alcohol/SMDI copolymer, *Phaseolus anguilaris* seed powder, *Polianthes tuberosa* extract, polyacrylate-3, polyacrylic acid, polycyclopentadiene, polyether-1, polyethylene/isopropyl maleate/MA copolyol, polyglyceryl-3 disiloxane dimethicone, polyglyceryl-3 polydimethylsiloxyethyl dimethicone, polymethacrylic acid, pokyquaternium-52, polyvinyl alcohol, potassium alginate, potassium aluminum polyacrylate, potassium carbomer, potassium carrageenan, potassium chloride, potassium palmate, potassium polyacrylate, potassium sulfate, potato starch modified, PPG-2 cocamide, PPG-1 hydroxyethyl caprylamide, PPG-2 hydroxyethyl cocamide, PPG-2 hydroxyethyl coco/isostearamide, PPG-3 hydroxyethyl soyamide, PPG-14 laureth-60 hexyl dicarbamate, PPG-14 laureth-60 isophoryl dicarbamate, PPG-14 palmeth-60 hexyl dicarbamate, propylene glycol alginate, PVP/decene copolymer, PVP montmorillonite, *Pyrus cydonia* seed, *Pyrus malus* (Apple) fiber, rhizobian gum, ricebranamide DEA, ricinoleamide DEA, ricinoleamide MEA, ricinoleamide MIPA, ricinoleamidopropyl betaine, ricinoleic acid/adipic acid/AEEA copolymer, *rosa* multiflora flower was, sclerotium gum, sesamide DEA, sesamidopropyl betaine, sodium acrylate/acryloyldimethyl taurate copolymer, sodium acrylates/acrolein copolymer, sodium acrylates/acrylonitrogens copolymer, sodium acrylates copolymer, sodium acrylates crosspolymer, sodium acrylates/vinyl isodecanoate crosspolymer, sodium acrylate/vinyl alcohol copolymer, sodium carbomer, sodium carboxymethyl chitin, sodium carboxymethyl dextran, sodium carboxymethyl beat-glucan, sodium carboxymethyl starch, sodium carrageenan, sodium cellulose sulfate, sodium chloride, sodium cyclodextrin sulfate, sodium hydroxypropyl starch phosphate, sodium isooctylene/MA copolymer, sodium magnesium fluorosilicate, sodium oleate, sodium palmitate, sodium palm kernelate, sodium polyacrylate, sodium polyacrylate starch, sodium polyacryloyldimethyl taurate, sodium polygammaglutamate, sodium polymethyacrylate, sodium polystyrene sulfonate, sodium silicoaluminate, sodium starch octenylsuccinate, sodium stearate, sodium stearoxy PG-hydroxyethylcellulose sulfonate, sodium styrene/acrylates copolymer, sodium sulfate, sodium tallowate, sodium tauride acrylates/acrylic acid/acrylonitrogens copolymer, sodium tocopheryl phosphate, *Solanum tuberosum* (potato) starch soyamide DEA, soyamidopropyl betaine, starch/acrylates/acrylamide copolymer, starch hydroxypropyltrimonium chloride, stearamide AMP stearamide DEA, stearamide DEA-distearate, stearamide DIBA-stearate, stearamide MEA, stearamide MEA-stearate, stearamide MIPA, stearamidopropyl betaine, steareth-60 cetyl ether, steareth-100/PEG-136/HDI copolymer, stearyl alcohol, stearyl betaine, *Sterculia urens* gum, synthetic fluorphlogopite, tallamide DEA, tallow alcohol, tallowamide DEA, tallowamide MEA, tallowamidopropyl betaine, tallowamidopropyl hydroxysultaine, tallowamine oxide, tallow betaine, tallow dihydroxylethyl betaine, *Tamarindus indica* seed gum, tapioca starch, TEA-alginate, TEA-carbomer, TEA-hydrochlorite, trideceth-2 carboxamide MEA, tridecyl alcohol, triethylene glycol dibenzoate, trimethyl pentanol hydroxyethyl ether, *triticum vulgare* (Wheat) germ powder, *triticum vulgare* (Wheat) kernel flour, *triticum vulgare* (Wheat) starch, tromethamine acrylates/acrylonitrogens copolymer, tromethamine magnesium aluminum silicate, undecyl alcohol, undecyulenamide DEA, undecylenamide MEA, undecylenamdopropyl betaine, welan gum, wheat germamide DEA, wheat germamidopropyl betaine, xanthan gum, yeast beta-glucan, yeast polysaccharides, *Zea mays* (Corn) starch, and combinations thereof.

The gelling agents are suitably present in the gelled composition in an amount of from about 0.1% (by weight gelled composition) to about 30% (by weight gelled composition). More suitably, the gelling agents are present in the gelled composition in an amount of from about 0.5% (by weight gelled composition) to about 10% (by weight gelled composition), and even more suitably, from about 1% (by weight gelled composition) to about 7% (by weight gelled composition).

In addition to the supersaturated solution and the gelling agent (if present), the composition can optionally comprise a plasticizer. As the supersaturated solution crystallizes, the wipe can become stiff and inflexible. As such, a plasticizer can be added to increase flexibility. Suitable plasticizers can include, for example, mineral oil, glycerine, soaps, fatty acids, sands, and combinations thereof. The plasticizer can be present in the composition in an amount of from about 0.1% (by weight composition) to about 30% (by weight composition). More suitably, the plasticizer can be present in the gelled composition in an amount of from about 1% (by weight composition) to about 10% (by weight composition).

Additionally, the composition can optionally include an emulsifying agent in combination with a plasticizer to ensure that the plasticizer is sufficiently dispersed within the composition. One particularly suitable emulsifying agent includes polysorbate 20. Additional suitable emulsifying agents are described in the International Cosmetic Ingredient Dictionary and Handbook, 10th Edition (2004), vol. 3 on pages 2276-2285, which is hereby incorporated by reference to the extent it is consistent. When an emulsifying agent is included in the composition, the emulsifying agent is present in the composition in an amount of from about 0.1% (by weight composition) to about 15% (by weight composition). More suitably, the emulsifying agent is present in the composition in an amount of from about 1% (by weight composition) to about 10% (by weight composition).

In addition to the compositions including a supersaturated solution (and any other optional ingredients), the wet wipes of the present disclosure include a core composition comprising one or more activation means to initiate crystallization of the supersaturated solution.

Typically, the activation means is comprised of one or more seed crystals having a similar chemistry as compared to the supersaturated solution. More particularly, a suitable activation means will have crystallographic data being within about 15% of that of the material to be crystallized in the supersaturated solution. As such, in the embodiment wherein the supersaturated solution is a supersaturated salt solution, the activation means is suitably a salt selected from the group consisting of sodium acetate, sodium sulfate, sodium sulfate decahydrate, sodium thiosulfate, potash alum, calcium nitrate, potassium acetate, ammonium nitrate, potassium nitrate, lithium acetate, magnesium acetate, chromium alum, sodium carbonate, magnesium sulfate, sodium borate, sodium bromide, sodium chromate, calcium chloride, magnesium chloride, magnesium nitrate, disodium phosphate, urea nitrate, and hydrates thereof. In the alternative embodiment, the supersaturated solution is a supersaturated sugar solution, wherein the activation means is suitably a sugar such as xylitol.

The activation means is suitably present in the core composition in an amount of from about 0.1% (by weight) to about 80% (by weight). More suitably, the activation means is present in the core composition in an amount of from about 0.1% (by weight) to about 50% (by weight), and even more suitably, from about 0.1% (by weight) to about 10% (by weight).

The activation means utilized in the core composition generally has a particle size of from about 0.01 micrometers to about 500 micrometers, desirably from about 1 micrometers to about 100 micrometers, desirably from about 5 micrometers to about 50 micrometers, and more desirably from about 10 micrometers to about 30 micrometers to facilitate substantial and continuous crystallization of the supersaturated solution. Although many activation means as described herein are commercially available in a number of particle sizes, it will be recognized by one skilled in the art that any number of techniques can be used to grind and produce the desired particle sizes.

Along with the activation means, a surfactant may optionally be included in the core composition. As used herein, "surfactant" is intended to include surfactants, dispersants, gelling agents, polymeric stabilizers, structurants, structured liquids, liquid crystals, Theological modifiers, grinding aids, defoamers, block copolymers, and combinations thereof. If a surfactant is utilized, it should be substantially non-reactive with the activation means. A surfactant may be added along with a activation means and a matrix material as described below to the core composition as a grinding and mixing aid for the activation means and to reduce the surface tension of the core composition and allow for better mixing with the supersaturated solution.

Any one of a number of surfactant types including anionic, cationic, nonionic, zwitterionic, and combinations thereof can be utilized in the core composition. One skilled in the art will recognize, based on the disclosure herein, that different activation means may benefit from one type of surfactant more than another; that is, the preferred surfactant for one chemistry may be different than the preferred surfactant for another. Particularly desirable surfactants will allow the core composition including the activation means and surfactant mixture to have a suitable viscosity for thorough mixing; that is, the surfactant will not result in the mixture having an undesirably high viscosity. Examples of commercially available surfactants suitable for use in the core composition include, for example, Antiterra 207 (BYK Chemie, Wallingford, Conn.) and BYK-P104 (BYK Chemie).

When included in the core composition, the surfactant is generally present in an amount of from about 0.01% (by weight core composition) to about 50% (by weight core composition), desirably from about 0.1% (by weight core composition) to about 25% (by weight core composition), more desirably from about 0.1% (by weight core composition) to about 10% (by weight core composition), more desirably from about 1% (by weight core composition) to about 5% (by weight core composition), and still more desirably about 1% (by weight core composition).

The core composition may optionally include a matrix material in addition to the activation means alone or in combination with the activation means and surfactant. The matrix material included in the core composition is used as a carrying or bulking agent for other components of the core composition, including, for example, the activation means. Specifically, the matrix material can provide for protection to the activation means throughout processing and transportation of the wet wipes. Although generally preferred to be a liquid material, the matrix material may also be a low melting material that is a solid at room temperature. The matrix material is desirably a material that is emulsifiable in water. Preferred liquid matrix materials include oils commonly used in commercial cosmetic applications that may impart some skin benefit to the user, such as a moisturizing or lubricating benefit. Generally, these oils are hydrophobic oils.

Specific examples of suitable liquid matrix materials include, for example, mineral oil, petrolatum, isopropyl myristate, silicones, copolymers such as block copolymers, waxes, butters, exotic oils, dimethicone, thermoionic gels, plant oils, animal oils, and combinations thereof. One preferred material for use as the matrix material is mineral oil. The matrix material is generally present in the core composition in an amount of from about 1% (by weight core composition) to about 99% (by weight core composition), desirably from about 10% (by weight core composition) to about 95% (by weight core composition), more desirably from about 15% (by weight core composition) to about 75% (by weight core composition), more desirably from about 20% (by weight core composition) to about 50% (by weight core composition), more desirably from about 25% (by weight core composition) to about 45% (by weight core composition), and even more desirably from about 30% (by weight core composition) to about 40% (by weight core composition).

As will be described in more detail below, in one embodiment, during the manufacturing process for the core composition, the contents of the core composition such as the activation means (and optionally, the matrix material and the surfactant) are introduced into a liquid solution such as a sodium alginate bath. During contact with this bath, it may be possible for the activation means present in the core composition to dissolve in the sodium alginate bath. This contact can result in a loss of potency and deactivation of the activation means and render the resulting core composition ineffective for its intended purpose. As such, in one embodiment of the present disclosure, the activation means included in the core composition is substantially completely surrounded by a wax material prior to being introduced into the core composition and ultimately into the sodium alginate bath. This wax material may provide the activation means with temporary protection during the timeframe of exposure to the sodium alginate bath; that is, the wax material may keep sodium alginate from contacting the activation means. Although the wax material provides protection of the activation means during creation of the core composition, in one embodiment it will gradually dissolve away and off of the activation means within the core composition over time; that is, the wax material dissolves into the matrix material of the core composition over time and off of the activation means so that the activation means can be directly contacted with the supersaturated solution upon activation in a wipe or other product.

In an alternative embodiment, the wax material does not substantially dissolve into the core composition and off of the activation means but is removed from the activation means at the time of use through shearing or disruption of the wax material; that is, the wax material is mechanically broken off of the activation means to allow the activation means access to the supersaturated solution.

It is generally desirable to have substantially complete coverage of the activation means with the wax material to ensure that the activation means is not susceptible to contact with the sodium alginate bath during the introduction of the core composition into the liquid as described herein. When contacted with a substantially continuous layer of wax material, the core composition including the activation means can be encapsulated in the liquid environment without the activation means losing potency. Generally, the wax material may be applied to the activation means in from about 1 to about 30 layers, desirably in from about 1 to about 10 layers.

Generally, the wax material is present on the activation means in an amount of from about 1% (by weight activation means) to about 50% (by weight activation means), desirably from about 1% (by weight activation means) to about 40% (by weight activation means), more desirably from about 1% (by weight activation means) to about 30% (by weight activation means), and even more desirably from about 1% (by weight activation means) to about 20% (by weight activation means). At these levels, there is sufficient wax material present on the activation means to provide the desired level of protection, yet not too much to keep it from dissolving over time into the core composition to allow for the supersaturated solution to access the activation means at the desired time.

Suitable wax materials for coating the heating agent are relatively low temperature melting wax materials. Although other low temperature melting materials can be used to coat the activation means in accordance with the present disclosure, low temperature melting wax materials are generally preferred. In one embodiment, the wax material has a melting temperature of less than about 140° C., desirably less than about 90° C. to facilitate the coating of the activation means as described below.

Suitable wax materials for use in coating the activation means include tetracosane, pentacosane, hexacosane, heptacosane, octacosane, glyceryl distearate, canola wax, hydrogenated cottonseed oil, hydrogenated soybean oil, castor wax, rapeseed wax, beeswax, carnauba wax, candelilla wax, microwax, polyethylene, polypropylene, epoxies, long chain alcohols, long chain esters, long chain fatty acids, hydrogenated plant oils, hydrogenated animal oils, microcrystalline waxes, metal stearates and metal fatty acids, and combinations thereof.

In one suitable embodiment, the core composition including the activation means alone or in combination with the matrix material and/or surfactant as described herein may include a number of layers. Specifically, the core composition includes an encapsulation layer completely surrounding the core composition, a moisture protective layer that surrounds the encapsulation layer, and a fugitive layer that surrounds the moisture protective layer. Each of these layers, each of which is optional, is more thoroughly discussed below.

When the core composition is surrounded by an encapsulation layer, the encapsulated core composition is desirably of a size such that, when incorporated into a personal care product such as a wet wipe, they cannot readily be felt on the skin by the user. Generally, the encapsulated core compositions have a diameter of from about 5 micrometers to about 10,000 micrometers, desirably from about 5 micrometers to about 5000 micrometers, desirably from about 50 micrometers to about 1000 micrometers, and still more desirably from about 300 micrometers to about 700 micrometers.

The encapsulation layer allows the core composition including the activation means to undergo further processing and use without a loss of structural integrity; that is, the encapsulation layer provides structural integrity to the core composition and its contents to allow for further processing.

In one embodiment, the encapsulation layer may be comprised of a polymeric material, a crosslinked polymeric material, a metal, a ceramic or a combination thereof, that results in a shell material that may be formed during manufacturing. Specifically, the encapsulation layer may be comprised of crosslinked sodium alginate, anionic dispersed latex emulsions, crosslinked polyacrylic acid, crosslinked polyvinyl alcohol, crosslinked polyvinyl acetate, silicates, carbonates, sulfates, phosphates, borates, polyvinyl pyrolidone, PLA/PGA, urea formaldehyde, melamine formaldehyde, polymelamine, crosslinked starch, nylon, ureas, hydrocolloids, clays, and combinations thereof. One particularly preferred crosslinked polymeric system is crosslinked sodium alginate.

The encapsulation layer present around the core composition generally has a thickness of from about 0.1 micrometers to about 500 micrometers, desirably from about 1 micrometer to about 100 micrometers, more desirably from about 1 micrometer to about 50 micrometers, more desirably from about 1 micrometer to about 20 micrometers, and even more desirably from about 10 micrometers to about 20 micrometers. At these thicknesses, the crosslinked polymeric layer has a sufficient thickness to provide its intended function. The encapsulation layer may be one discrete layer, or may be comprised of multiple layers added in one or more steps. Suitable methods for measuring the thickness of the encapsulation layer (once fractured), and the other optional layers described herein, include Scanning Electron Microscopy (SEM) and Optical Microscopy.

Generally, the encapsulation layer will be present in from about 1 layer to about 30 layers, desirably in from about 1 layer to about 20 layers, and more desirably in from about 1 layer to about 10 layers to provide further protection.

The core composition as described herein may optionally comprise a moisture protective layer surrounding the encapsulation layer to produce a substantially fluid-impervious encapsulated core composition. As used herein, "fluid" is meant to include both water (such as the supersaturated solution and other fluids) and oxygen (and other gases) such that "fluid-impervious" includes both water-impervious and oxygen-impervious. Although referred to throughout herein as a "moisture protective layer," one skilled in the art based on the disclosure herein will recognize that this layer may be both "moisture protective" and "oxygen protective;" that is, the layer will protect and insulate the core composition and its contents from both water and oxygen.

When present, the moisture protective layer substantially completely surrounds the encapsulation layer described above. The moisture protective layer will help to ensure that the core composition and its content (i.e., activation means) will not come into contact with the supersaturated solution and allow premature crystallization.

The moisture protective layer may be present over the encapsulation layer in one layer or in multiple layers. Desirably, the moisture protective layer will be present in from about 1 layer to about 30 layers, desirably in from about 1 layer to about 20 layers, and more desirably in from about 1 layer to about 10 layers to provide further protection. As noted above, the moisture protective layer substantially completely surrounds the encapsulation layer to keep the supersaturated solution from reaching the internal contents of the core composition and ultimately the activation means. To ensure the moisture protective layer substantially completely covers the encapsulation layer, multiple layers may be utilized as noted above. Each of the moisture protective layers generally has a thickness of from about 1 micrometer to about 200 micrometers, desirably from about 1 micrometer to about 100 micrometers, and even more desirably from about 1 micrometer to about 50 micrometers.

The moisture protective layer may comprise any number of materials including, for example, polyols in combination with isocynate, styrene-acrylate, vinyl toluene-acrylate, styrene-butadiene, vinyl-acrylate, polyvinyl butyral, polyvinyl acetate, polyethylene terephthalate, polypropylene, polystyrene, polymethyl methacrylate, poly lactic acid, polyvinylidene chloride, polyvinyldichloride, polyethylene, alkyl polyester, carnauba wax, hydrogenated plant oils, hydrogenated animal oils, fumed silica, silicon waxes, fluorinated chlorosilanes, ethoxy fluorochemicals, methoxyfluorochemicals, titanium dioxide, silicon dioxide, metals, metal carbonates, metal sulfates, ceramics, metal phosphates, microcrystalline waxes, and combinations thereof.

In addition to the moisture protective layer, the core composition may also optionally be surrounded by a fugitive layer that surrounds the moisture protective layer, if present, or the encapsulating layer if the moisture protective layer is not present. The fugitive layer can act to stabilize and protect the activation means from being exposed prematurely to the supersaturated solution due to mechanical load, or can provide other benefits. When present over the moisture protective layer (or encapsulation layer), the fugitive layer can impart strength and withstand a given mechanical load until a time when the fugitive layer is ruptured by the end user or is decomposed or degraded in a predictable manner in the supersaturated solution, usually during shipment and/or storage of the product prior to use. Consequently, the fugitive layer allows the activation means to survive relatively high mechanical load conditions commonly experienced in shipping and/or manufacturing.

In one embodiment, the fugitive layer substantially completely surrounds the moisture protective layer (or the encapsulating layer) such that there are substantially no access points to the underlying layer. Alternatively, the fugitive layer may be a non-continuous, porous or non-porous layer surrounding the moisture protective layer (or the encapsulating layer).

The fugitive layer, similar to the moisture protective layer, may be present in multiple layers. Specifically, the fugitive layer may be present in anywhere from about 1 to about 30 layers, desirably from about 1 to about 20 layers, and more desirably from about 1 to about 10 layers. Generally, each fugitive layer may have a thickness of from about 1 micrometer to about 200 micrometers, desirably from about 1 micrometer to about 100 micrometers, and more desirably from about 1 micrometer to about 50 micrometers.

The fugitive layer may be comprised of any one of a number of suitable materials including, for example, polymers of dextrose and other sugars, starches, alginate, acrylates, polyvinyl alcohol, ethylene oxide polymers, polyethyleneimine, gums, gum arabic, polyacrylamide, hydroxypropyl cellulose, hydroxypropyl methylcellulose, polyvinyl pyrrolidone, poly(2-acrylamido-2-methyl-1-propanesulfonic acid), poly(acrylamido-N-propyltrimethylammonium chloride), and combinations thereof. One particularly preferred material for use as the fugitive layer is starch.

In another embodiment, the encapsulated core composition can further be surrounded by petroleum such as petroleum jelly prior to being incorporated into the product to gel the core composition in a particular region of the product. It should be recognized that other gelatinous hydrophobic materials such as soft waxes with low melting points may also be used in combination with or in place of the petroleum jelly. Specifically, the petroleum jelly layer can prevent the core composition from moving in the product and prematurely contacting the supersaturated solution. Suitably, the core composition is surrounded from about 300% (by weight core composition) to about 100,000% (by weight core composition) petroleum jelly. One particularly preferred petroleum jelly for surrounding the core composition is Vaseline® Petroleum Jelly.

In another embodiment, the petroleum jelly surrounds the activation means prior to the activation means being incorporated into the core composition. Suitably, the activation means is surrounded by the petroleum jelly in an amount of from about 1000% (by weight activation means) to about 1,000,000% (by weight activation means) petroleum jelly.

The encapsulated core composition as described herein may be manufactured in any number of ways as discussed below. The first step in the manufacturing process is generally to coat the desired activation means (e.g., sodium acetate) with a wax material as described above prior to incorporating the wax material-coated activation means into the core composition. As would be recognized by one skilled in the art based on the disclosure herein, this wax material coating of the activation means step is optional and can be eliminated if such a coating is not desired and the activation means is to be incorporated into the core composition without any protective coating.

In one embodiment, the wax material is coated onto the activation means by blending the activation means and wax material together at an elevated temperature sufficient to melt the wax material in the presence of the activation means and the melted wax material and activation means stirred sufficiently to coat the activation means. After the coating of the activation means is complete, the mixture is allowed to cool to room temperature to allow the wax to solidify on the activation means. After the coated activation means have cooled, they can be ground to the desired size prior to incorporation into the core composition.

After the grinding of the wax material-coated activation means, it may be desirable to subject the ground material to a further process to ensure that the wax material coating is substantially complete around the activation means. Suitable additional processes include, for example, spheroidization (high heat fluidization slightly below the melt temperature of the wax material) and ball milling. These additional processes can be used to ensure substantially complete coverage of the activation means with the wax material.

The wax material-coated (or uncoated) activation means can be used alone in the core composition or can be mixed with the other optional ingredients in the core composition, including the matrix material, surfactant, and encapsulating activator (as described more fully below). As will be further recognized by one skilled in the art, some methods of forming an outer layer on the core composition (i.e., coacervation) may not require a chemical encapsulating activator to be present in the core composition, but may utilize a change in pH, a change in temperature, and/or a change in ionic strength of the liquid solution to initiate the formation of the encapsulating layer around the core composition. Additionally, it will be further recognized by one skilled in the art based on the disclosure herein that the encapsulating activator, when present, may be located outside of the core composition; that is, the encapsulating activator may be located in the liquid solution for example, although it is generally desirable to have it located within the core composition.

The encapsulating activator, when present in the core composition, can act as a crosslinking agent to crosslink the encapsulating layer discussed herein. Once the core composition is introduced into a liquid solution containing a crosslinkable compound as described below, the encapsulating activator interacts with the crosslinkable compound and causes it to crosslink on the outer surface of the composition to form a crosslinked shell. Because the encapsulating activator chemically reacts with the crosslinkable compound contained in the liquid solution, the resulting encapsulated core composition may not contain any encapsulating activator in its final form.

The encapsulating activator may be any activator capable of initiating a crosslinking reaction in the presence of a crosslinkable compound. Suitable encapsulating activators include, for example, polyvalent ions of calcium, polyvalent ions of copper, polyvalent ions of barium, silanes, aluminum, titanates, chelators, acids, and combinations thereof. Specifically, the encapsulating activator may be calcium chloride, calcium sulfate, calcium oleate, calcium palmitate, calcium stearate, calcium hypophosphite, calcium gluconate, calcium formate, calcium citrate, calcium phenylsulfonate, and combinations thereof. A preferred encapsulating activator is calcium chloride.

The encapsulating activator is generally present in the core composition in an amount of from about 0% (by weight core composition) to about 25% (by weight core composition), desirably from about 0.1% (by weight core composition) to about 15% (by weight core composition), and still more desirably from about 0.1% (by weight core composition) to about 10% (by weight composition).

To produce the core composition including the activation means (which may or may not be surrounded by a wax material), matrix material, encapsulating activator and surfactant (if any), the desired amounts of these components may be optionally passed through a milling device that serves to thoroughly mix the components together for further processing. Suitable wet milling operations include, for example, bead milling and wet ball milling. Additionally, processes known to those skilled in the art such as hammer milling and jet milling may be used to first prepare the activation means, and then disperse the treated activation means into the core composition containing the matrix material, surfactant and encapsulating activator followed by thorough mixing.

Once the core composition is prepared, it is introduced into a liquid solution, generally held at room temperature, to activate a crosslinking reaction to form an outer encapsulating shell that protects the core composition and its components (core material) and allows for immediate use or further processing. Although described herein primarily in reference to a "crosslinking reaction," it will be recognized by one skilled in the art based on the disclosure herein that the encapsulation layer can be formed around the core composition not only by a crosslinking reaction, but also by coacervation, coagulation, flocculation, adsorption, complex coacervation and self-assembly, all of which are within the scope of the present disclosure. As such, the term "crosslinking reaction" is meant to include these other methods of forming the encapsulation layer around the core composition.

One particular advantage of one embodiment described herein is that the presence of the encapsulating activator in the core composition allows for almost instantaneous crosslinking when the core composition is introduced into the solution containing the crosslinkable compound; this reduces the potential for unwanted heating agent deactivation. In one embodiment, the core composition is added dropwise into the liquid containing the crosslinkable compound and the beads that form when the drops contact the liquid are kept separated during the crosslinking reaction using a sufficient amount of stirring and mixing. It is preferred to use sufficient stirring and mixing to keep the beads separate during the crosslinking reaction to ensure that they remain separate, individual beads and do not form larger agglomerated masses that are susceptible to numerous defects. Generally, the drops added to the liquid solution can have a diameter of from about 0.05 millimeters to about 10 millimeters, desirably from about 0.1 millimeter to about 3 millimeters, and still more desirably from about 0.5 millimeters to about 1 millimeter. Alternatively, the core composition may be introduced or poured into the liquid solution including the crosslinkable compound and then subjected to shear sufficient to break the paste into small beads for crosslinking thereon.

In one embodiment, the liquid solution includes a crosslinkable compound that can be crosslinked in the presence of the encapsulating activator to form the outer encapsulate shell. Optionally, a surfactant as described herein can also be introduced into the liquid solution to facilitate crosslinking. When the core composition including the encapsulating activator is introduced into the liquid containing the crosslinkable compound, the encapsulating activator migrates to the interface between the core composition and the liquid solution and initiates the crosslinking reaction on the surface of the core composition to allow the encapsulation layer to grow outward toward the liquid solution. The thickness of the resulting encapsulation layer surrounding the core composition can be controlled by (1) controlling the amount of encapsulating activator included in the core composition; (2) controlling the amount of time the core composition including the encapsulating activator is exposed to the liquid solution including the crosslinkable compound; and/or (3) controlling the amount of crosslinkable compound in the liquid solution. Generally, an encapsulating layer of sufficient and desired thickness can be formed around the core composition by allowing the core composition to dwell in the liquid solution including the crosslinkable compound for from about 10 seconds to about 40 minutes, desirably from about 5 minutes to about 30 minutes, and still more desirably from about 10 minutes to about 20 minutes.

It is generally desirable that the liquid solution containing the crosslinkable compound has a viscosity suitable for allowing sufficient mixing of the formed beads therein; that is, the viscosity of the liquid solution should not be so high that stirring and mixing is substantially impaired and the ability to keep the formed beads separated reduced. To that end, the liquid solution containing the crosslinkable compound generally contains from about 0.1% (by weight liquid solution) to about 50% (by weight liquid solution), desirably from about 0.1% (by weight liquid solution) to about 25% (by weight liquid solution) and more desirably from about 0.1% (by weight liquid solution) to about 1% (by weight liquid solution) crosslinkable compound.

Any number of crosslinkable compounds can be incorporated into the liquid solution to form the encapsulated layer around the core composition upon contact with the encapsulating activator. Some suitable crosslinkable compounds include, for example, sodium alginate, anionic dispersed latex emulsions, polyacrylic acid, polyvinyl alcohol, polyvinyl acetate, silicates, carbonates, sulfates, phosphates, borates, and combinations thereof. A particularly desirable crosslinkable compound is sodium alginate.

Once a sufficient amount of time has passed for the encapsulating layer to form on the core composition, the formed beads may be removed from the liquid including the crosslinkable compound. The resulting encapsulated core composition may optionally be washed several times to remove any crosslinkable compound thereon and dried and are then ready for use or for further processing. One suitable washing liquid is deionized water.

In one embodiment, the encapsulated core composition formed as described above is subjected to a process to impart a moisture protective layer thereon that surrounds the encapsulated layer that comprises the crosslinked compound. This moisture protective layer provides the encapsulated core composition with increased protection from the supersaturated solution; that is, it makes the encapsulated core composition substantially fluid impervious and allows the encapsulated core composition to survive long term in the supersaturated solution environment and not degrade until the moisture protective layer is ruptured by mechanical action. The moisture protective layer may be a single layer applied onto the encapsulated core composition, or may comprise several layers one on top of the other.

The moisture protective layer may be applied to the encapsulated core composition utilizing any number of suitable processes including, for example, atomizing or dripping a moisture protective material onto the encapsulated core composition. Additionally, a Wurster coating process may be utilized. When a solution is used to provide the moisture protective coating, the solids content of the solution is generally from about 0.1% (by weight solution) to about 70% (by weight solution), desirably from about 1% (by weight solution) to about 60% (by weight solution), and still more desirably from about 5% (by weight solution) to about 40% (by weight solution). Generally, the viscosity of the solution (at 25° C.) including the moisture protective material is from about 0.6 centipoise to about 10,000 centipoise, desirably from about 20 centipoise to about 400 centipoise, and still more desirably from about 20 centipoise to about 100 centipoise.

In one specific embodiment, a fluidized bed process is utilized to impart the moisture protective layer on the encapsulated core composition. The fluidized bed is a bed or layer of encapsulated core composition capsules through which a stream of heated or unheated carrier gas is passed at a rate sufficient to set the encapsulated capsules in motion and cause them to act like a fluid. As the capsules are fluidized, a spray of a solution comprising a carrier solvent and the moisture protective material is injected into the bed and contacts the capsules imparting the moisture protective material thereon. The treated capsules are collected when the desired moisture protective layer thickness is achieved. The capsules can be subjected to one or more fluidized bed processes to impart the desired level of moisture protective layer.

In another embodiment, the encapsulated core composition, which may or may not include a moisture protective layer as described above, is subjected to a process for imparting a fugitive layer thereon surrounding the outermost layer. For example, if the encapsulated core composition includes a moisture protective layer, the fugitive layer would be applied on the capsule such that it substantially completely covered the moisture protective layer. The fugitive layer can be applied in a single layer, or may be applied in multiple layers.

The fugitive layer may be applied to the encapsulated core composition utilizing any number of suitable processes including, for example, atomizing or dripping a fugitive material onto the encapsulated core composition. When a solution is used to provide the fugitive coating, the solids content of the solution is generally from about 1% (by weight solution) to about 70% (by weight solution), desirably from about 10% (by weight solution) to about 60% (by weight solution). The pH of the solution is generally from about 2.5 to about 11. Generally, the viscosity of the solution (at 25° C.) including the fugitive material is from about 0.6 centipoise to about 10,000 centipoise, desirably from about 20 centipoise to about 400 centipoise, and still more desirably from about 20 centipoise to about 100 centipoise. Similar to the moisture protective layer, a preferred method of applying the fugitive layer utilizes a fluidized bed reactor. Also, a Wurster coating process may also be used.

As noted above, the supersaturated solutions and the activation means as described herein are suitable for use in a number of products, including wipe products, wraps, such as medical wraps and bandages, headbands, wristbands, helmet pads, personal care products, and the like. Although described primarily herein in relation to wipes, it will be recognized by one skilled in the art that the supersaturated solutions and activation means described herein could be incorporated into any one or more of the other products listed above.

Generally, the wipes of the present disclosure including the supersaturated solutions and activation means can be wet wipes or dry wipes. As used herein, the term "wet wipe" means a wipe that includes greater than about 70% (by weight substrate) moisture content. As used herein, the term "dry wipe" means a wipe that includes less than about 10% (by weight substrate) moisture content. Specifically, suitable wipes for use in the present disclosure can include wet wipes, hand wipes, face wipes, cosmetic wipes, household wipes, industrial wipes, and the like. Particularly preferred wipes are wet wipes, and other wipe-types that include a solution.

Materials suitable for the substrate of the wipes are well know to those skilled in the art, and are typically made from a fibrous sheet material which may be either woven or nonwoven. For example, suitable materials for use in the wipes may include nonwoven fibrous sheet materials which include meltblown, coform, air-laid, bonded-carded web materials, hydroentangled materials, and combinations thereof. Such materials can be comprised of synthetic or natural fibers, or a combination thereof. Typically, the wipes of the present disclosure define a dry basis weight of from about 25 grams per square meter to about 120 grams per square meter and desirably from about 40 grams per square meter to about 90 grams per square meter.

In one particular embodiment, the wipes of the present disclosure comprise a coform basesheet material of polymer fibers and absorbent fibers having a basis weight of from about 60 to about 80 grams per square meter and desirably about 75 grams per square meter. Such coform basesheets are manufactured generally as described in U.S. Pat. Nos. 4,100,324, issued to Anderson, et al. (Jul. 11, 1978); 5,284,703, issued to Everhart, et al. (Feb. 8, 1994); and 5,350,624, issued to Georger, et al. (Sep. 27, 1994), which are incorporated by reference to the extent to which they are consistent herewith. Typically, such coform basesheets comprise a gas-formed matrix of thermoplastic polymeric meltblown fibers and cellulosic fibers. Various suitable materials may be used to provide the polymeric meltblown fibers, such as, for example, polypropylene microfibers. Alternatively, the polymeric meltblown fibers may be elastomeric polymer fibers, such as those provided by a polymer resin. For instance, Vistamaxx® elastic olefin copolymer resin designated VM2380, available from ExxonMobil Corporation (Houston, Tex.) or KRATON G-2755, available from Kraton Polymers (Houston, Tex.) may be used to provide stretchable polymeric meltblown fibers for the coform basesheets. Other suitable polymeric materials or combinations thereof may alternatively be utilized as known in the art.

As noted above, the coform basesheet material additionally may comprise various absorbent cellulosic fibers, such as, for example, wood pulp fibers. Suitable commercially available cellulosic fibers for use in the coform basesheets can include, for example, NF 405, which is a chemically treated bleached southern softwood Kraft pulp, available from Weyerhaeuser Co. of Federal Way (Washington); NB 416, which is a bleached southern softwood Kraft pulp, available from Weyerhaeuser Co.; CR-0056, which is a fully debonded softwood pulp, available from Bowater, Inc. (Greenville, S.C.); Golden Isles 4822 debonded softwood pulp, available from Koch Cellulose (Brunswick, Ga.); and SULPHATATE HJ, which is a chemically modified hardwood pulp, available from Rayonier, Inc. (Jesup, Ga.).

The relative percentages of the polymeric meltblown fibers and cellulosic fibers in the coform basesheet material can vary over a wide range depending upon the desired characteristics of the wipes. For example, the coform basesheet material may comprise from about 10 weight percent to about 90 weight percent, desirably from about 20 weight percent to about 60 weight percent, and more desirably from about 25 weight percent to about 35 weight percent of the polymeric meltblown fibers based on the dry weight of the coform basesheet being used to provide the wipes.

In an alternative embodiment, the wipes of the present disclosure can comprise a composite which includes multiple layers of materials. For example, the wipes may include a multi-layer composite which includes one or more elastomeric films or meltblown layers between two coform layers as described above. In such a configuration, the coform layers may define a basis weight of from about 15 grams per square meter to about 30 grams per square meter and the elastomeric layer(s) may include a film material such as a polyethylene metallocene film. Such composites are manufactured generally as described in U.S. Pat. No. 6,946,413, issued to Lange, et al. (Sep. 20, 2005), which is hereby incorporated by reference to the extent it is consistent herewith.

In accordance with the present disclosure, the composition including the supersaturated solution is capable of generating heat to produce a warming sensation in the wipe upon being contacted with the contents (i.e., activation means) of the core composition.

In one embodiment, the wipe is a wet wipe comprising a wetting solution in addition to the fibrous sheet material, the composition including the supersaturated solution, and the core composition including the activation means. The wetting solution can be any wetting solution known to one skilled in the wet wipe art. Generally, the wetting solution can include water, emollients, surfactants, preservatives, chelating agents, pH adjusting agents, skin conditioners, fragrances, and combinations thereof. For example, one suitable wetting solution for use in the wet wipe of the present disclosure comprises about 98% (by weight) water, about 0.6% (by weight) surfactant, about 0.3% (by weight) humectant, about 0.3% (by weight) emulsifier, about 0.2% (by weight) chelating agent, about 0.35% (by weight) preservative, about 0.002% (by weight) skin conditioning agent, about 0.03% (by weight) fragrance, and about 0.07% (by weight) pH adjusting agent. One specific wetting solution suitable for use in the wet wipe of the present disclosure is described in U.S. Pat. No. 6,673,358, issued to Cole et al. (Jan. 6, 2004), which is incorporated herein by reference to the extent it is consistent herewith.

It has been determined that the ideal temperature for a wipe to be utilized is a temperature of from about 30° C. to about 40° C. (86° F.-104° F.). A conventional wipe will typically be stored at room temperature (about 23° C. (73.4° F.). As such, when the core composition ruptures, and releases the activation means, and the activation means contacts the supersaturated solution, a warming sensation is produced, increasing the temperature of the solution and wipe by at least about 5° C. More suitably, the temperature of the solution and wipe is increased by at least about 10° C., even more suitably, increased by at least about 15° C., and even more suitably increased by at least about 20° C. or more.

Generally, the elapsed time between the dispensing of a wipe product and use of the product is about 2 seconds or less, and typically is about 6 seconds or less. As such, once the core composition of the present disclosure is ruptured and the activation means is contacted with the supersaturated solution, the crystallization reaction begins to generate heat and a warming sensation is suitably perceived in less than about 20 seconds. More suitably, the warming sensation is perceived in less than about 10 seconds, even more suitably, in less than about 5 seconds, and even more suitably, in less than about 2 seconds.

Additionally, once the warming sensation begins, the warming sensation of the wipe product is suitably maintained for at least about 5 seconds. More suitably, the warming sensation is maintained for at least about 8 seconds, even more suitably for at least about 15 seconds, even more suitably for at least about 20 seconds, even more suitably for at least about 40 seconds, and even more suitably for at least about 1 minute.

To generate the temperature increase described above, the wipes of the present disclosure suitably comprise at least about 3.0 grams per square meter composition including the supersaturated solution, and a core composition including at least one activation means. More suitably, the wipes comprise at least about 30 grams per square meter composition including supersaturated solution, and a core composition including at least about 10 activation means, and, even more suitably, at least about 100 grams per square meter composition including supersaturated solution, and a core composition including at least about 100 activation means.

In the embodiment, where the composition including the supersaturated solution is in a first fluid-impermeable pouch and the core composition including the activation means is in a second fluid-impermeable pouch (as more fully described below), the first fluid-impermeable pouch suitably comprises at least about 3.0 grams per square meter composition of supersaturated solution, and the second fluid-impermeable pouch comprises a core composition including at least one activation means. More suitably, the first fluid-impermeable pouch comprises at least about 30 grams per square meter composition, and the second fluid-impermeable pouch comprises a core composition including at least about 10 activation means, and, even more suitably, the first fluid-impermeable pouch comprises at least about 100 grams per square meter composition including supersaturated solution, and the second fluid-impermeable pouch comprises a core composition including at least about 100 activation means.

In the embodiment where the supersaturated solution is in a gelled composition, the wipe suitably comprises at least about 3.00 grams per square meter gelled composition, and a core composition including at least one activation means. More suitably, the wipes comprise at least about 30 grams per square meter gelled composition, and a core composition including at least about 10 activation means, and, even more suitably, at least about 100 grams per square meter gelled composition, and a core composition including at least about 100 activation means.

As noted above, the supersaturated solution is present in the composition in an amount of from about 70% (by weight composition) to about 99.9% (by weight composition). More suitably, the supersaturated solution is present in the composition in an amount of from about 90% (by weight composition) to about 99.5% (by weight composition), and even more suitably, from about 93% (by weight composition) to about 99% (by weight composition).

The supersaturated solutions and core compositions including the activation means can be applied to the basesheet material of a wipe using any means known to one skilled in the art. Preferably, both the supersaturated solution and the core composition are embedded within one or more fluid-impermeable layers such as a film; the fluid-impermeable layers being enclosed by one or more basesheet materials laminated to the outside of the fluid-impermeable layers. By embedding the core composition within the core of a multi-layer wipe, the wipe will have a reduced grittiness feel because of a cushion effect and the ruptured shells of the core composition will not come into direct contact with the user's skin. Additionally, when the core composition is located between two or more layers, the activation means are better protected from premature contact with the supersaturated solution and heat release caused by the conditions of manufacturing, storage, and transportation of the wipe.

Moreover, by embedding the supersaturated solution within the core of the multi-layer wipe, the supersaturated solution is not diluted by the wet wipe solution, and further, less evaporation of supersaturated solution can occur. This allows for an optimal concentration of the supersaturated solution to warm the wipe effectively as described above. Furthermore, the supersaturated solution typically has a high solids content and can leave residue on the surface of a user's skin. The residue can cause irritation and/or an odor. As such, by embedding the solution, there is less residue left on the skin by the supersaturated solution.

In one embodiment, both the supersaturated solution and the core composition including the activation means are entrapped between a first fluid-impermeable layer and a second fluid-impermeable layer. While in this embodiment the wipe suitably comprises two fluid-impermeable layers, it should be understood that the wipe can suitably comprise three fluid-impermeable layers, even more suitably four fluid-impermeable layers, and even more suitably five or more fluid-impermeable layers. In one embodiment, the layers are separate layers. In another embodiment, the layers are plied together.

Suitable fluid-impermeable include film materials such as polyethylene films having a thickness of from about 0.008 millimeters (0.3 mil) to about 0.051 millimeters (2.0 mil). Other suitable film materials include, for example, polyethylene, polypropylene, and polylactic acid. The film can include 48-60% (by weight) linear low density polyethylene and 38-50% (by weight) calcium carbonate particulates that may be uniformly dispersed and extruded into the film. Another example of a suitable film can be a PMP-1 material, which is available from Mitsui Toatsu Chemicals, Inc., a company having offices in Tokyo, Japan; or an XKO-8044 polyolefin film available from 3M Company of Minneapolis, Minn. Other suitable films include copolymers of polypropylene and polyethylene, and polyester.

To incorporate the supersaturated solution and the core composition including the activation means in between the layers of fluid-impermeable material, the supersaturated solution and core composition are sandwiched between a first layer and a second layer of the fluid-impermeable material, and the layers are then laminated together using any means known in the art. For example, the layers can be secured together thermally or by a suitable laminating adhesive composition.

Thermal bonding includes continuous or discontinuous bonding using a heated roll. Point bonding is one suitable example of such a technique. Thermal bonds should also be understood to include various ultrasonic, microwave, and other bonding methods wherein the heat is generated in the film.

In a preferred embodiment, the first layer and second layer are laminated together using a water insoluble adhesive composition. Suitable water insoluble adhesive compositions can include hot melt adhesives and latex adhesives as described in U.S. Pat. Nos. 6,550,633, issued to Huang, et al. (Apr. 22, 2003); 6,838,154, issued to Anderson, et al. (Oct. 25, 2005); and 6,958,103, issued to Varona et al. (Jan. 4, 2005), which are hereby incorporated by reference to the extent they are consistent herewith. Suitable hot melt adhesives can include, for example, RT 2730 APAO and RT 2715 APAO, which are amorphous polyalphaolefin adhesives (commercially available from Huntsman Polymers Corporation, Odessa, Tex.) and H2800, H2727A, and H2525A, which are all styrenic block copolymers (commercially available from Bostik Findley, Inc., Wauwatosa, Wis.). Suitable latex adhesives include, for example, DUR-O-SET E-200 (commercially available from National Starch and Chemical Co., Ltd., Bridgewater, N.J.) and Hycar 26684 (commercially available from B. F. Goodrich, Laval, Quebec). Typically, the adhesive composition can be applied to the desired area by spraying, knifing, roller coating, or any other means suitable in the art for applying adhesive compositions.

Suitably, the adhesive composition can be applied to the desired area of the fluid-impermeable material in an amount of from about 0.01 grams per square meter to about 20 grams per square meter. More suitably, the adhesive composition can be applied in an amount of from about 0.05 grams per square meter to about 0.5 grams per square meter.

Figure 2A:
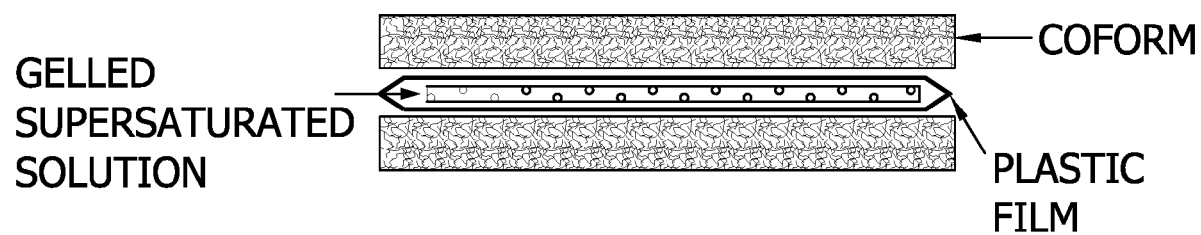
FIG. 2A is a side view of a wet wipe comprising a gelled composition comprising a supersaturated solution and an activation means being entrapped between two film layers as disclosed in one embodiment of the present disclosure.
Figure 2B:
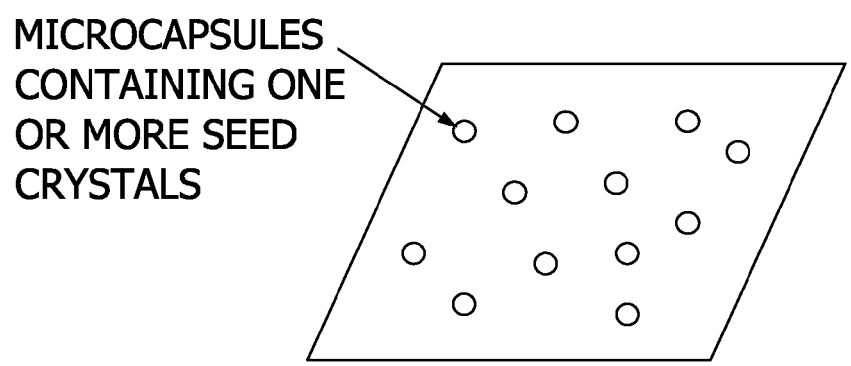
FIG. 2B is a top view of the gelled composition including the supersaturated solution and activation means of the wet wipe depicted in FIG. 2A.

In one embodiment, as depicted in FIGS. 2A and 2B, the supersaturated solution is combined with a gelling agent to form a gelled composition as discussed herein above. Specifically, by forming a gelled composition, the supersaturated solution can be evenly distributed between the fluid-impermeable layers. Specifically, the gelled composition prevents the supersaturated solution from pooling in one or more discreet areas of the wipe.

Figure 1B:
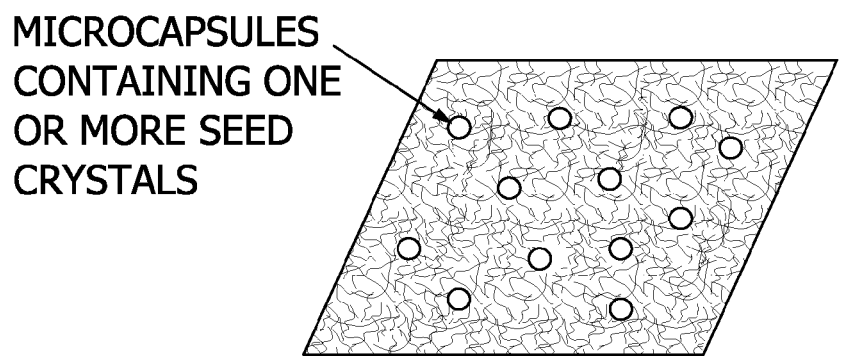
FIG. 1B is a top view of the fibrous sheet material including the supersaturated solution and activation means of the wet wipe depicted in FIG. 1A.

In another embodiment, as shown in FIGS. 1A and 1B, the supersaturated solution is absorbed into a fibrous sheet material and the core composition is deposited on an outer surface of the fibrous sheet material prior to being entrapped between the first fluid-impermeable layer and the second fluid-impermeable layer. Similar to the gelled composition embodiment, the fibrous sheet allows for an even distribution of supersaturated solution between the fluid-impermeable layers. The fibrous sheet material may typically be either woven or nonwoven. For example, suitable materials for use in the wipes may include nonwoven fibrous sheet materials which include meltblown, coform, air-laid, bonded-carded web materials, hydroentangled materials, and combinations thereof. Such materials can be comprised of synthetic or natural fibers, or a combination thereof. Generally, the fibrous sheet material will have a dry thickness of from about 0.02 mm to about 0.80 mm, more suitably, from about 0.05 mm to about 0.30 mm, and even more suitably, from about 0.1 mm to about 0.2 mm. As used herein, "dry thickness" refers to the thickness of the fibrous sheet material prior to adding the supersaturated solution and core composition.

To provide for better attachment of the core composition to the outer surface of the fibrous sheet material, a water insoluble adhesive composition can be applied with the core composition onto the outer surface of the fibrous sheet material. Suitable water insoluble adhesive compositions are described herein above. Suitably, the adhesive composition can be applied to the outer surface of the fibrous sheet material in an amount of from about 0.01 grams per square meter to about 20 grams per square meter. More suitably, the adhesive composition can be applied in an amount of from about 0.05 grams per square meter to about 0.5 grams per square meter.

Additionally, the fibrous sheet material can be cut into various patterns prior to incorporating the supersaturated solution and core composition. By using a patterned fibrous sheet material, a targeted warming sensation can be achieved. These patterned fibrous sheet materials can additionally reduce manufacturing costs as reduced amounts of supersaturated solution and core composition are required. Suitably, the fibrous sheet material can be cut into patterns including, for example, characters, an array of separate lines, swirls, numbers, or dots of supersaturated solution or core composition. Continuous patterns, such as stripes or separate lines that run parallel with the machine direction of the web, are particularly preferred as these patterns may be more process-friendly.

One or more basesheet materials are then laminated to the outside surfaces of the fluid-impermeable layers described above. Specifically, a first basesheet material can be laminated to the outside surface of the first fluid-impermeable layer and a second basesheet material can be laminated to the outside surface of the second fluid-impermeable layer. The layers can be secured together thermally or by a suitable laminating adhesive composition as described above for laminating the fluid-impermeable layers together.

Materials suitable for the basesheet material of the wipes are well know to those skilled in the art, and are typically made from a fibrous sheet material which may be either woven or nonwoven as described above. Typically, the wipes of the present disclosure define a dry basis weight of from about 25 grams per square meter to about 120 grams per square meter and desirably from about 40 grams per square meter to about 90 grams per square meter. As used herein, "dry basis weight" refers to the weight of the fibrous sheet material prior to incorporating the supersaturated solution and core composition therein.

In one particular embodiment, the wipes of the present disclosure comprise one or more coform basesheets of polymer fibers and absorbent fibers having a basis weight of from about 60 to about 80 grams per square meter and desirably about 75 grams per square meter. Such coform basesheets are manufactured generally as described in U.S. Pat. Nos. 4,100,324, issued to Anderson, et al. (Jul. 11, 1978); 5,284,703, issued to Everhart, et al. (Feb. 8, 1994); and 5,350,624, issued to Georger, et al. (Sep. 27, 1994), which are incorporated by reference to the extent in which they are consistent herewith. Typically, such coform basesheets comprise a gas-formed matrix of thermoplastic polymeric meltblown fibers and cellulosic fibers. Various suitable materials may be used to provide the polymeric meltblown fibers, such as, for example, polypropylene microfibers. Alternatively, the polymeric meltblown fibers may be elastomeric polymer fibers, such as those provided by a polymer resin. For instance, Vistamaxx® elastic olefin copolymer resin designated VM2380, available from ExxonMobil Corporation (Houston, Tex.) or KRATON G-2755, available from Kraton Polymers (Houston, Tex.) may be used to provide stretchable polymeric meltblown fibers for the coform basesheets. Other suitable polymeric materials or combinations thereof may alternatively be utilized as known in the art.

As noted above, the coform basesheet materials additionally may comprise various absorbent cellulosic fibers, such as, for example, wood pulp fibers. Suitable commercially available cellulosic fibers for use in the coform basesheets can include, for example, NF 405, which is a chemically treated bleached southern softwood Kraft pulp, available from Weyerhaeuser Co. of Federal Way (Washington); NB 416, which is a bleached southern softwood Kraft pulp, available from Weyerhaeuser Co.; CR-0056, which is a fully debonded softwood pulp, available from Bowater, Inc. (Greenville, S.C.); Golden Isles 4822 debonded softwood pulp, available from Koch Cellulose (Brunswick, Ga.); and SULPHATATE HJ, which is a chemically modified hardwood pulp, available from Rayonier, Inc. (Jesup, Ga.).

The relative percentages of the polymeric meltblown fibers and cellulosic fibers in the coform basesheet can vary over a wide range depending upon the desired characteristics of the wipes. For example, the coform basesheet may comprise from about 20 weight percent to about 50 weight percent, desirably from about 15 weight percent to about 40 weight percent, and more desirably from about 25 weight percent to about 35 weight percent of the polymeric meltblown fibers based on the dry weight of the coform basesheet being used to provide the wipes.

When the basesheet material is a meltblown material, the basesheet material can suitably be made up of two meltblown layers secured together, more suitably three meltblown layers, even more suitably four meltblown layers, and even more suitably five or more meltblown layers. When the basesheet material is a coform material, the basesheet material can suitably be made up of two coform basesheet layers secured together, more suitably three coform basesheet layers, even more suitably four coform basesheet layers, even more suitably five or more coform basesheet layers.

In yet another embodiment, the supersaturated solution and core composition including the activation means may be independently distributed within one or more pouches of fluid-impermeable material and then the pouch or pouches can be embedded within the basesheet material as described above. It should be noted that when there is only one pouch, the supersaturated solution and core composition should remain separated by being contained in separate compartments within the pouch.

Figure 3A:
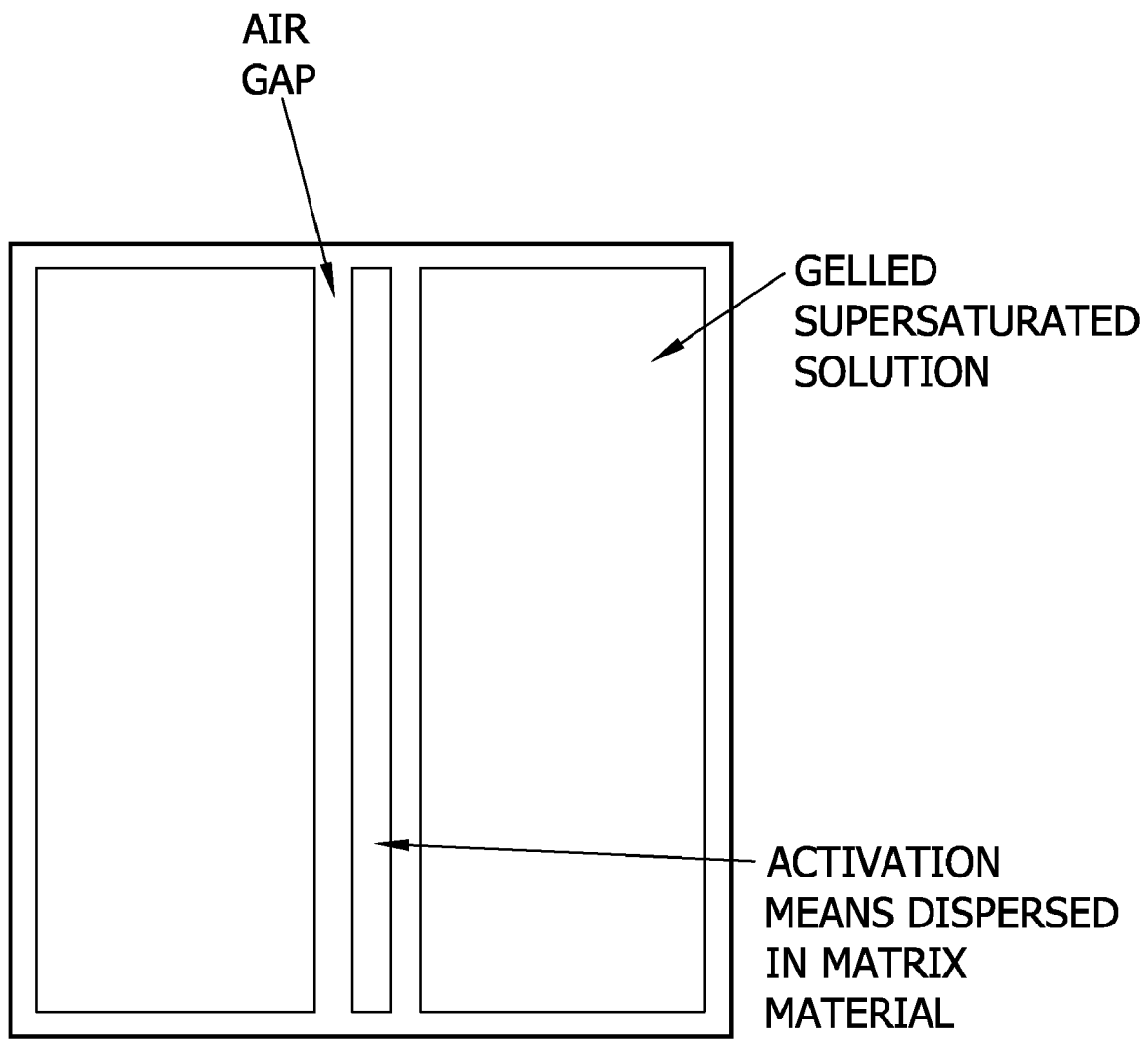
FIG. 3A is a side view of a wet wipe comprising a gelled composition comprising a supersaturated solution, and a powdered activation means dispersed in a pouch, wherein the gelled composition is separated from the activation means by air as disclosed in one embodiment of the present disclosure.
Figure 3B:
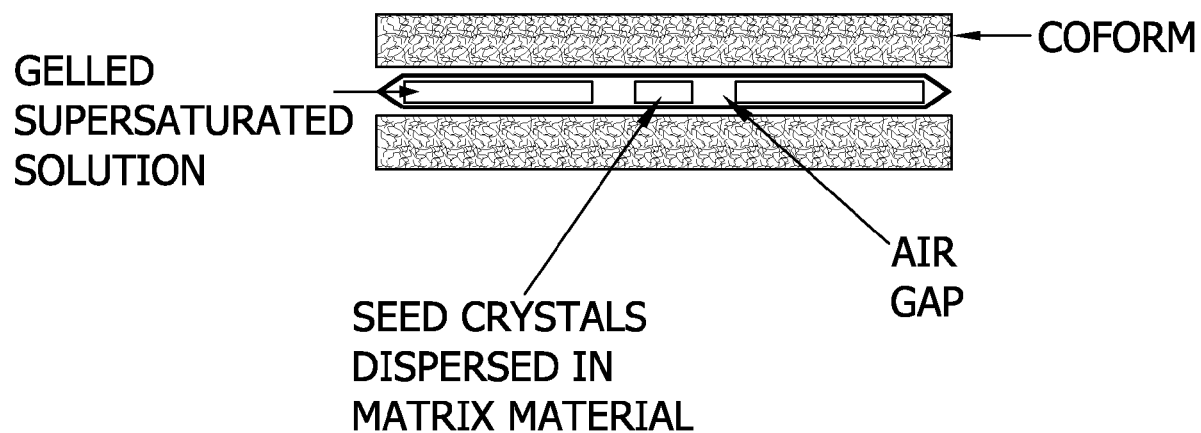
FIG. 3B is an end view of the pouch containing the gelled composition and the activation means of the wet wipe depicted in FIG. 3A.

In one preferred embodiment, as shown in FIGS. 3A and 3B, the supersaturated solution is gelled using a gelling agent and the gelled composition is incorporated into a single pouch with the core composition including the activation means. The gelled composition and the core composition are separated by air. In this embodiment, the core composition can be surrounded by petroleum jelly (or another gelatinous hydrophobic material) to gel the core composition in between the air gaps and gelled composition. In one particularly preferred embodiment, the core composition is surrounded by from about 300% (by weight core composition) to about 100,000% (by weight core composition) Vaseline® Petroleum Jelly.

Figure 4B:
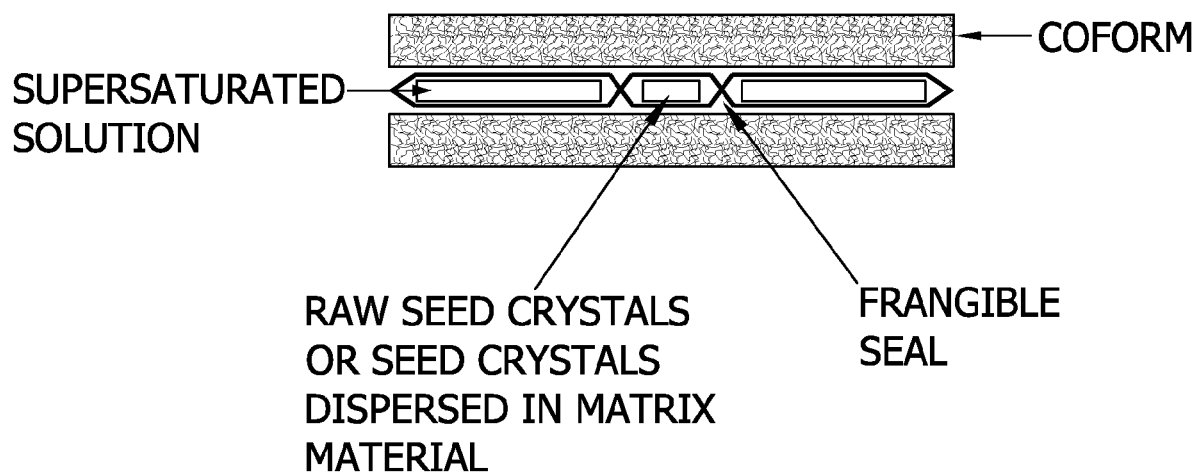
FIG. 4B is an end view of the pouches containing the supersaturated solution and the strip including the activation means of the wet wipe depicted in FIG. 4A.

In another preferred embodiment, as shown in FIGS. 4A and 4B, the supersaturated solution can be incorporated into a first fluid-impermeable pouch and the core composition including the activation means can be incorporated into a second fluid-impermeable pouch. The pouches or compartments of a single pouch are then separated by a sealed seam defined by thermally sealed facing regions of the fluid-impermeable material. It should be understood that the term "seal" is meant to encompass all types of pouch opening configurations, including perforated tear lines, scored lines, tear zones, etc. The seal is preferably a "frangible seal" that can be ruptured by application of a manual compression of the pouch; thus allowing the confined supersaturated solution of one pouch or compartment to commingle with the core composition of another pouch or compartment.

The fluid-impermeable pouches are comprised of the fluid-impermeable materials such as the film materials described herein above. Specifically, to produce a fluid-impermeable pouch, the fluid-impermeable material (e.g., film) is folded at a fold axis such that the first end is folded towards the second end to define at least a portion of a front panel of the pouch. Once folded, the aligned lateral sides of the fluid-impermeable material define lateral edges of the pouch. Three sides of the pouch are then thermally sealed using methods such as a conventional heated bonding roll. The bonding parameters, such as temperature, dwell time, etc., may be readily empirically determined by those skilled in the art as a function of the type of film material, processing speed, desired seal strength, and so forth. Also, the bonding pattern may be any one or combination of suitable patterns.

In one embodiment, the frangible seal in between the first and second fluid-impermeable pouches or separate compartments of one fluid-impermeable pouch can suitably be formed by heat-sealing two superimposed multilayer sheets of fluid-impermeable material each having an innermost sealing layer made from a resin. Suitable resins include blends of one or more polyolefins such as polyethylene including metallocene polyethylene with polybutylene or polypropylene including homopolymer or copolymers thereof (specifically, polyethylene/polybutylene blends and polyethylene/polypropylene blends), polypropylene with polybutylene; polypropylene with ethylene methacrylic acid copolymer, and polypropylene with styrene-ethylene/butylene-styrene block terpolymer. For example, in one specific embodiment, one side of the pouch described above is superimposed and heat sealed using a resin.

In order to manufacture a frangible seal containing at least one force concentrating means for selectively exceeding the seal strength of the frangible seal various methodologies are contemplated. Preferably, shape and/or curvature of the frangible seal are to be employed to advantageously concentrate the forces created when the pouch is manually compressed or squeezed. Also, the geometry and/or variable width of the heated seal employed to heat seal the frangible seal can be employed to produce a force concentrating means useful in the present disclosure.

For purposes of measuring seal strength, 4 inch×6 inch samples of the fluid-impermeable material are to be cut with the long side of the samples in the machine direction of the fluid-impermeable material. Enough film samples are cut to provide one set of three specimens for each heat seal condition. The samples then are folded so that the sealant layer of each side contacts the other. The sample is then heat sealed between the jaws of the heat sealer at the appropriate temperature, time and pressure. The heat-sealed samples are then conditioned for at least 24 hours at 73° F. (22.8° C.) and 50% relative humidity before testing. The folded over portion of the sealed fluid-impermeable material is cut in half, forming suitable flaps to be placed in the Instron jaw clamps. One inch specimens are then cut in the machine direction of the fluid-impermeable material to provide at least three 1 inch wide test specimens at each set of sealing conditions.

The seal strength is measured by pulling the seals apart in the machine direction of the fluid-impermeable material using the Instron at 5 inches/minute jaw speed. The maximum force required to cause the seal to fail is then recorded, and the average of at least three specimens is reported in grams/inch. Suitably, the seal strength of the frangible seal utilized is from about 10 grams/inch to about 3,000 grams/inch.

When using separate pouches or compartments within a single pouch, the supersaturated solution can optionally be combined with a gelling agent to form a gelled composition as discussed herein above at the time of or prior to being incorporated into the pouch or compartment.

Additionally, the core composition may be colored using a coloring agent prior to applying the core composition to the wipe. The coloring of the core composition can improve the aesthetics of the wipe. Additionally, in embodiments where targeted warming is desired, the coloring of the core composition can direct the consumer of the wipe product to the location of the core composition in the wipe.

Suitable coloring agents include, for example, dyes, color additives, and pigments or lakes. Suitable dyes include, for example, Blue 1, Blue 4, Brown 1, External Violet 2, External Violet 7, Green 3, Green 5, Green 8, Orange 4, Orange 5, Orange 10, Orange 11, Red 4, Red 6, Red 7, Red 17, Red 21, Red 22, Red 27, Red 28, Red 30, Red 31, Red 33, Red 34, Red 36, Red 40, Violet 2, Yellow 5, Yellow 6, Yellow 7, Yellow 8, Yellow 10, Yellow 11, Acid Red 195, Anthocyanins, Beetroot Red, Bromocresol Green, Bromothymol Blue, Capsanthin/Capsorubin, Curcumin, and Lactoflavin. Also, many dyes found suitable for use in the European Union and in Japan may be suitable for use as coloring agents in the present disclosure.

Suitable color additives include, for example, aluminum powder, annatto, bismuth citrate, bismuth oxychloride, bronze powder, caramel, carmine, beta carotene, chloraphyllin-copper complex, chromium hydroxide green, chromium oxide greens, copper powder, disodium EDTA-copper, ferric ammonium ferrocyanide, ferric ferrocyanide, guauazulene, guanine, henna, iron oxides, lead acetate, manganese violet, mica, pyrophylite, silver, titanium dioxide, ultramarines, zinc oxide, and combinations thereof.

Suitable pigments or lakes include, for example, Blue 1 Lake, External Yellow 7 Lake, Green 3 Lake, Orange 4 Lake, Orange 5 Lake, Orange 10 Lake, Red 4 Lake, Red 6 Lake, Red 7 Lake, Red 21 Lake, Red 22 Lake, Red 27 Lake, Red 28 Lake, Red 30 Lake, Red 31 Lake, Red 33 Lake, Red 36 Lake, Red 40 Lake, Yellow 5 Lake, Yellow 6 Lake, Yellow 7 Lake, Yellow 10 Lake, and combinations thereof.

Any means known to one of skill in the art capable of producing sufficient force to break the encapsulated core composition can be used in the present disclosure. In one embodiment, the encapsulated core composition can be broken by the user at the point of dispensing the wipe from a package. For example, a mechanical device located inside of the package containing the wipes can produce a rupture force sufficient to rupture the capsules upon dispensing the wipe, thereby exposing the contents (i.e., activation means) of the core composition to the supersaturated solution.

In another embodiment, the capsules can be broken by the user just prior to or at the point of use of the wipe. By way of example, in one embodiment, the force produced by the hands of the user of the wipe can break the capsules, exposing the contents of the core composition.

In one specific embodiment, a product including the supersaturated solution and core composition as described herein can additionally suitably include a biocide agent for use in cleaning.

Using the supersaturated solution and core composition in the product in combination with the biocide agents results in an increased biocidal effect when the supersaturated solution is contacted with the activation means and heat is generated. Specifically, the increase in temperature has been found to activate or enhance the function of the biocide agents present in the cleansing product.

Generally, the three main factors affecting the efficacy of biocide agents include: (1) mass transfer of biocide agents in the cleansing product to the microbe-water interface; (2) chemisorption of biocide agents to the cell wall or cell membrane of the microbes; and (3) diffusion of the activated chemisorbed biocide agent into the cell of the microbe. It has been found that temperature is a primary regulator of all three factors. For example, the lipid bilayer cell membrane structure of many microbes "melts" at higher than room temperatures, allowing holes to form in the membrane structure. These holes can allow the biocide agent to more easily diffuse through the microbe cell wall or membrane and enter the cell.

Generally, the cleansing products of the present disclosure are capable of killing or substantially inhibiting the growth of microbes. Specifically, the biocide agent of the cleansing products interfaces with either the reproductive or metabolic pathways of the microbes to kill or inhibit the growth of the microbes.

Microbes suitably affected by the biocide agents of the cleansing products include viruses, bacteria, fungi, and protozoans. Viruses that can be affected by the biocide agents include, for example, Influenza, Parainfluenza, Rhinovirus, Human Immunodeficiency Virus, Hepatitis A, Hepatitis B, Hepatitis C, Rotavirus, Norovirus, Herpes, Coronavirus, and Hanta virus. Both gram positive and gram negative bacteria are affected by the biocide agents of the cleansing composition. Specifically, bacteria affected by the biocide agents used in the cleansing compositions include, for example, *Staphylococcus aureus, Streptococcus pneumoniae, Streptococcus pyogenes, Pseudomonas aeruginose, Klebsiella pneumoniae, Escherichia coli, Enterobacter aerogenes, Enterococcus faecalis, Bacillus subtilis, Salmonella typhi, Mycobacterium tuberculosis*, and *Acinetobacter baumannii*. Fungi affected by the biocide agents include, for example, *Candida albicans, Aspergillus niger*, and *Aspergillus* fumigates. Protozoans affected by the biocide agents include, for example, *cyclospora cayetanensis, Cryptosporidum parvum*, and species of microsporidum.

Suitable biocide agents for use in the cleansing products include, for example, isothiazolones, alkyl dimethyl ammonium chloride, triazines, 2-thiocyanomethylthio benzothiazol, methylene bis thiocyanate, acrolein, dodecylguanidine hydrochloride, chlorophenols, quarternary ammonium salts, gluteraldehyde, dithiocarbamates, 2-mercaptobenzothiazole, para-chloro-meta-xylenol, silver, chlorohexidine, polyhexamethylene biguanide, n-halamines, triclosan, phospholipids, alpha hydroxy acids, 2,2-dibromo-3-nitrilopropionamide, 2-bromo-2-nitro-1,3-propanediol, farnesol, iodine, bromine, hydrogen peroxide, chlorine dioxide, alcohols, ozone, botanical oils (e.g., tee tree oil and rosemary oil), botanical extracts, benzalkonium chloride, chlorine, sodium hypochlorite, and combinations thereof.

The cleansing products of the present disclosure may also optionally contain a variety of other components which may assist in providing the desired cleaning properties. For example, additional components may include non-antagonistic emollients, surfactants, preservatives, chelating agents, pH adjusting agents, fragrances, moisturizing agents, skin benefit agents (e.g., aloe and vitamin E), antimicrobial actives, acids, alcohols, or combinations or mixtures thereof. The products may also contain lotions, and/or medicaments to deliver any number of cosmetic and/or drug ingredients to improve performance.

Typically, to manufacture the wet wipe with the biocide agent, the biocide agent can be applied to the outer layers of the wipe or, alternatively, added to the wet wipe solution and applied to the wipe.

In another embodiment, the biocide agents can be microencapsulated in a shell material prior to being introduced into or onto the wipe. Generally, the biocide agent can be microencapsulated using any method known in the art. Suitable microencapsulation shell materials include cellulose-based polymeric materials (e.g., ethyl cellulose), carbohydrate-based materials (e.g., cationic starches and sugars) and materials derived therefrom (e.g., dextrins and cyclodextrins) as well as other materials compatible with human tissues.

The microencapsulation shell thickness may vary depending upon the biocide agent utilized, and is generally manufactured to allow the encapsulated formulation or component to be covered by a thin layer of encapsulation material, which may be a monolayer or thicker laminate layer, or may be a composite layer. The microencapsulation layer should be thick enough to resist cracking or breaking of the shell during handling or shipping of the product. The microencapsulation layer should also be constructed such that atmospheric conditions during manufacturing, storage, and/or shipment will not cause a breakdown of the microencapsulation layer and result in a release of the biocide agent.

Microencapsulated biocide agents applied to the outer surface of the wipes as discussed above should be of a size such that the user cannot feel the encapsulated shell on the skin during use. Typically, the capsules have a diameter of no more than about 25 micrometers, and desirably no more than about 10 micrometers. At these sizes, there is no "gritty" or "scratchy" feeling on the skin when the wipe is utilized.

Suitably, the biocide agent is present in the wet wipe in an amount of suitably 0.001 grams per square meter to about 50 grams per square meter. More suitably, the biocide agent is present in the wet wipe in an amount of from about 0.002 grams per square meter to about 25 grams per square meter, and even more suitably, in an amount of from about 0.002 grams per square meter to about 4.0 grams per square meter.

The present disclosure is illustrated by the following examples which are merely for the purpose of illustration and are not to be regarded as limiting the scope of the disclosure or manner in which it may be practiced.

EXAMPLE 1

In this example, a sample of supersaturated salt solution was evaluated for its ability to generate heat upon being contacted with an activation means.

To produce the supersaturated salt solution, about 12 grams of a solution of sodium acetate, having approximately 53% (by weight) sodium acetate and having a temperature of 90-100° C. (194-212° F.), was poured onto a 7.5 inch×7.0 inch sheet (basis weight of about 33 grams/meter$^2$) of Scott® Paper toweling (available from Kimberly-Clark, Neenah, Wis.). The toweling was then placed into a Hefty Slide-Rite polyethylene bag (available from Pactiv Corporation, Lake Forest, Ill.) and the bag was boiled for a few seconds. The bag was then allowed to cool.

Once cooled, the bag was opened and an agglomeration of seed crystals of sodium acetate (about 1 mm in size) was placed onto the sheet of toweling. Crystallization initiated and there was a perceived heating effect. The crystallization continued for approximately 40 seconds.

EXAMPLE 2

In this example, a sample of a gelled composition including supersaturated salt solution was evaluated for its ability to generate heat upon being contacted with an activation means.

To produce the gelled composition, 10% (by weight) fumed silica having a particle size of about 0.014 microns, was mixed with 90% (by weight) supersaturated sodium acetate salt solution available from ProHeat® Reusable Handwarmer packs (available from Prism Enterprises, Inc., San Antonio, Tex.). Approximately 5.0 grams of the resulting gelled composition were then placed into a Hefty Slide-Rite polyethylene bag (available from Pactiv Corporation, Lake Forest, Ill.).

An agglomeration of seed crystals of sodium acetate (approximately 1 mm in size) was placed against the gelled composition inside the bag. Crystallization initiated and there was a perceived heating effect. The crystallization continued for approximately 50 seconds, producing a stiff solid crystallized product.

EXAMPLE 3

In this Example, a gelled composition including a supersaturated salt solution was packaged with a powder of seed crystals in a pouch, wherein the gelled composition and seed crystals were separated by air. The pouch was squeezed manually to allow the contents of the pouch to commingle and the ability of the supersaturated salt solution to generate heat once contacted with the seed crystals was evaluated.

A first mixture of a gelled composition was produced by mixing 6.3% (by weight) fumed silica with 93.7% (by weight) ProHeat® sodium acetate solution. A second mixture was formed from 10% (by weight) sodium acetate powder and 90% (by weight) Vaseline® Petroleum Jelly.

The first mixture of gelled composition was placed into a polyethylene bag in two separate locations. The second mixture containing the seed crystals was placed in a stripe in between the two areas containing the first mixture. When the polyethylene films of the bag were pinched and moved between fingers of the tester, the first mixture contacted the second mixture and crystallization was initiated in multiple locations. As crystallization continued, heat was generated.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A wet wipe comprising a composition comprising a supersaturated solution, and a core composition surrounded by an encapsulation layer, the core composition comprising a matrix material and an activation means.

2. The wet wipe as set forth in claim 1 wherein the composition is present in the wet wipe in an amount of from about 3.0 grams per square meter to about 850 grams per square meter.

3. The wet wipe as set forth in claim 1 wherein the supersaturated solution is a supersaturated salt solution prepared from an aqueous solution of a salt, the salt being selected from the group consisting of sodium acetate, sodium sulfate, sodium thiosulfate, potash alum, calcium nitrate, potassium acetate, ammonium nitrate, potassium nitrate, lithium acetate, magnesium acetate, chromium alum, sodium carbonate, magnesium sulfate, sodium borate, sodium bromide, sodium chromate, calcium chloride, magnesium chloride, magnesium nitrate, disodium phosphate, urea nitrate, and hydrates thereof.

4. The wet wipe as set forth in claim 1 wherein the supersaturated solution is a supersaturated sugar solution prepared from an aqueous solution of a sugar, the sugar being xylitol.

5. The wet wipe as set forth in claim 1 wherein the supersaturated solution is present in the composition in an amount of from about 70% (by weight) to about 99.9% (by weight).

6. The wet wipe as set forth in claim 1 wherein the composition further comprises a plasticizer.

7. The wet wipe as set forth in claim 6 wherein the composition further comprises an emulsifying agent in combination with the plasticizer.

8. The wet wipe as set forth in claim 1 wherein the activation means is selected from the group consisting of sodium acetate, sodium sulfate, sodium sulfate decahydrate, sodium thiosulfate, potash alum, calcium nitrate, potassium acetate, ammonium nitrate, potassium nitrate, lithium acetate, magnesium acetate, chromium alum, sodium carbonate, magnesium sulfate, sodium borate, sodium bromide, xylitol, sodium chromate, calcium chloride, magnesium chloride, magnesium nitrate, disodium phosphate, urea nitrate, and hydrates thereof.

9. The wet wipe as set forth in claim 1 wherein the activation means is present in the core composition in an amount of from about 0.1% (by weight core composition) to about 80% (by weight core composition).

10. The wet wipe as set forth in claim 1 further comprising a moisture protective layer surrounding the encapsulation layer.

11. The wet wipe as set forth in claim 10 further comprising a fugitive layer surrounding the moisture protective layer.

12. The wet wipe as set forth in claim 1 wherein upon contact between the supersaturated solution and the activation means, the temperature of the wet wipe is increased by at least about 5° C. in less than about 20 seconds.

13. The wet wipe as set forth in claim 12 wherein the increased temperature of the wet wipe is maintained for at least about 5 seconds.

14. The wet wipe as set forth in claim 1 wherein the composition is a gelled composition and the gelled composition comprises a gelling agent in combination with the supersaturated solution.

15. The wet wipe as set forth in claim 14 wherein the gelled composition is present in the wet wipe in an amount of from about 3.0 grams per square meter to about 850 grams per square meter.

16. The wet wipe as set forth in claim 14 wherein the gelling agent is selected from the group consisting of fumed silica and laponite clay.

17. The wet wipe as set forth in claim 1 further comprising a first fluid-impermeable pouch and a second fluid-impermeable pouch, wherein the first fluid-impermeable pouch comprises the composition comprising the supersaturated solution and the second fluid-impermeable pouch comprises the core composition comprising the matrix material and activation means.

18. The wet wipe as set forth in claim 17 wherein the first fluid-impermeable pouch and second fluid-impermeable pouch are connected by a frangible seal.

19. The wet wipe as set forth in claim 1 further comprising a fibrous sheet material, the fibrous sheet material comprising the composition comprising the supersaturated solution.

20. A method of producing a wipe comprising:
encapsulating an activation means within a core composition; and
incorporating a composition comprising a supersaturated solution, and the core composition within a basesheet material.

* * * * *

UNITED STATES PATENT AND TRADEMARK OFFICE
CERTIFICATE OF CORRECTION

PATENT NO. : 7,597,954 B2
APPLICATION NO. : 11/610970
DATED : October 6, 2009
INVENTOR(S) : Amundson et al.

It is certified that error appears in the above-identified patent and that said Letters Patent is hereby corrected as shown below:

In the Specification, Column 10, row 56, delete "Theological" and insert therefore --rheological--.

Signed and Sealed this

Twenty-second Day of December, 2009

David J. Kappos
*Director of the United States Patent and Trademark Office*